(12) United States Patent
Van et al.

(10) Patent No.: US 8,329,199 B2
(45) Date of Patent: *Dec. 11, 2012

(54) COMPOSITIONS THAT INCLUDE A HYDROPHOBIC COMPOUND AND A POLYAMINO ACID CONJUGATE

(75) Inventors: Sang Van, San Diego, CA (US);
Yucheng Song, Salt Lake City, UT (US);
Xinghe Wang, San Diego, CA (US);
Zheng Hou, San Diego, CA (US);
Zhongling Feng, San Diego, CA (US);
Gang Zhao, Vista, CA (US); Lei Yu,
Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/475,672

(22) Filed: May 18, 2012

(65) Prior Publication Data

US 2012/0230917 A1    Sep. 13, 2012

Related U.S. Application Data

(63) Continuation of application No. 12/117,601, filed on May 8, 2008, now Pat. No. 8,197,828.

(60) Provisional application No. 60/916,903, filed on May 9, 2007.

(51) Int. Cl.
*A61K 9/00* (2006.01)

(52) U.S. Cl. .................. 424/400; 424/78.08; 424/78.17

(58) Field of Classification Search .................. None
See application file for complete search history.

(56) References Cited

U.S. PATENT DOCUMENTS

| | | | |
|---|---|---|---|
| 4,675,381 A | 6/1987 | Bichon et al. |
| 4,738,843 A | 4/1988 | Oguchi et al. |
| 4,745,161 A | 5/1988 | Saudek et al. |
| 4,888,398 A | 12/1989 | Bichon et al. |
| 4,892,733 A | 1/1990 | Bichon et al. |
| 4,925,662 A | 5/1990 | Oguchi et al. |
| 4,976,962 A | 12/1990 | Bichon et al. |
| 5,087,616 A | 2/1992 | Myers et al. |
| 5,219,564 A | 6/1993 | Zalipsky et al. |
| 5,372,807 A | 12/1994 | Poiani et al. |
| 5,384,333 A | 1/1995 | Davis et al. |
| 5,385,738 A | 1/1995 | Yamahira et al. |
| 5,412,072 A | 5/1995 | Sakurai et al. |
| 5,439,686 A | 8/1995 | Desai et al. |
| 5,449,513 A | 9/1995 | Yokoyama et al. |
| 5,449,720 A | 9/1995 | Russell-Jones et al. |
| 5,455,027 A | 10/1995 | Zalipsky et al. |
| 5,470,510 A | 11/1995 | Willey et al. |
| 5,498,421 A | 3/1996 | Grinstaff et al. |
| 5,510,103 A | 4/1996 | Yokoyama et al. |
| 5,548,064 A | 8/1996 | Russell-Jones et al. |
| 5,660,822 A | 8/1997 | Poiani et al. |
| 5,693,751 A | 12/1997 | Sakurai et al. |
| 5,720,950 A | 2/1998 | Poiani et al. |
| 5,738,864 A | 4/1998 | Schacht et al. |
| 5,762,909 A | 6/1998 | Uzgiris |
| 5,770,222 A | 6/1998 | Unger et al. |
| 5,869,466 A | 2/1999 | Russell-Jones et al. |
| 5,871,710 A | 2/1999 | Bogdanov et al. |
| 5,871,747 A | 2/1999 | Gengoux-Sedlik et al. |
| 5,876,698 A | 3/1999 | Schmitt-Willich et al. |
| 5,900,228 A | 5/1999 | Meade et al. |
| 5,929,198 A | 7/1999 | Tang |
| 5,977,163 A | 11/1999 | Li et al. |
| 5,980,862 A | 11/1999 | Meade et al. |
| 5,981,564 A | 11/1999 | Pagé et al. |
| 6,004,763 A | 12/1999 | Gengoux et al. |
| 6,030,941 A | 2/2000 | Summerton et al. |
| 6,096,331 A | 8/2000 | Desai et al. |
| 6,136,846 A | 10/2000 | Rubinfeld et al. |
| 6,143,817 A | 11/2000 | Hallam et al. |
| 6,229,009 B1 | 5/2001 | Lambert et al. |
| 6,235,264 B1 | 5/2001 | Uzgiris |
| 6,251,866 B1 | 6/2001 | Prakash et al. |
| 6,262,107 B1 | 7/2001 | Li et al. |
| 6,306,865 B1 | 10/2001 | Pendergast et al. |
| 6,326,021 B1 | 12/2001 | Schwendeman et al. |
| 6,358,919 B1 | 3/2002 | Kanie et al. |
| 6,391,336 B1 | 5/2002 | Royer |
| 6,395,254 B1 | 5/2002 | Sinn et al. |
| 6,441,025 B2 | 8/2002 | Li et al. |
| 6,441,026 B1 | 8/2002 | Bissery |
| 6,497,901 B1 | 12/2002 | Royer |
| 6,506,405 B1 | 1/2003 | Desai et al. |
| 6,515,017 B1 | 2/2003 | Li et al. |
| 6,517,824 B1 | 2/2003 | Kohn et al. |
| 6,521,209 B1 | 2/2003 | Meade et al. |

(Continued)

FOREIGN PATENT DOCUMENTS

CN   14448420   10/2003

(Continued)

OTHER PUBLICATIONS

Alm et al., "Effects of topically applied PGF2 alpha and its isopropylester on normal and glaucomatous human eyes," *Prog. Clin. Biol. Res.* (1989) 312:447-58.

Asano, et al., "Fusibility of Poly(n-carboxy α-Amino Acid Anhydride) Materials Treated under Pressure-Heat Conditions and in Vitro-in Vivo Degradation of Hot-Pressed Materials," *J. Macromol. Sci-Chem.*, (1984) A21(5): 561-582.

Beverung, et al., "Adsorption dynamics of L-glutamic acid copolymers at a heptane/water interface." *Biophysical Chemistry*, (1998) 70:121-132.

Blout, et al., "Polypeptides. III. The Synthesis of High Molecular Weight Poly-(-benzyl-L-glutamates," *J. Am. Chem. Soc.*, (1956) 78(5):941-946 (1956).

(Continued)

*Primary Examiner* — James Rogers
(74) *Attorney, Agent, or Firm* — Knobbe Martens Olson & Bear LLP

(57) ABSTRACT

Various compositions that include a hydrophobic compound and a polyamino acid conjugate are prepared. The compositions described herein are useful for a variety of drug, biomolecule, and imaging agent delivery applications.

20 Claims, 5 Drawing Sheets

U.S. PATENT DOCUMENTS

| | | |
|---|---|---|
| 6,528,061 B1 | 3/2003 | Phalipon et al. |
| 6,537,579 B1 | 3/2003 | Desai et al. |
| 6,630,486 B1 | 10/2003 | Royer |
| 6,673,347 B1 | 1/2004 | Offord et al. |
| 6,693,083 B2 | 2/2004 | Prakash et al. |
| 6,713,045 B1 | 3/2004 | Meade et al. |
| 6,716,452 B1 | 4/2004 | Piccariello et al. |
| 6,730,699 B2 | 5/2004 | Li et al. |
| 6,749,868 B1 | 6/2004 | Desai et al. |
| 6,753,006 B1 | 6/2004 | Desai et al. |
| 6,762,188 B1 | 7/2004 | Pendergast et al. |
| 6,855,695 B2 | 2/2005 | Lin et al. |
| 6,884,817 B2 | 4/2005 | Li et al. |
| 6,939,538 B2 | 9/2005 | Prescott et al. |
| 6,962,707 B2 | 11/2005 | Schenk |
| 6,995,245 B2 | 2/2006 | Pool |
| 7,060,724 B2 | 6/2006 | Li et al. |
| 7,067,618 B1 | 6/2006 | Kato et al. |
| 7,070,797 B2 | 7/2006 | Pardee et al. |
| 7,153,864 B2 | 12/2006 | Bhatt et al. |
| 7,317,070 B1 | 1/2008 | Ponnusamy |
| 2001/0028876 A1 | 10/2001 | Uzgiris et al. |
| 2001/0028877 A1 | 10/2001 | Uzgiris |
| 2001/0041189 A1 | 11/2001 | Xu |
| 2002/0016285 A1 | 2/2002 | Bhatt et al. |
| 2002/0077279 A1 | 6/2002 | Kumar et al. |
| 2002/0077290 A1 | 6/2002 | Bhatt et al. |
| 2002/0123609 A1 | 9/2002 | Frechet et al. |
| 2002/0183243 A1 | 12/2002 | Bhatt et al. |
| 2002/0187202 A1 | 12/2002 | Goswami et al. |
| 2002/0197261 A1 | 12/2002 | Li et al. |
| 2003/0049253 A1 | 3/2003 | Li et al. |
| 2003/0054977 A1 | 3/2003 | Kumar et al. |
| 2003/0073617 A1 | 4/2003 | Li et al. |
| 2003/0113335 A1 | 6/2003 | Li et al. |
| 2003/0114363 A1 | 6/2003 | Li et al. |
| 2003/0114397 A1 | 6/2003 | Li et al. |
| 2003/0114518 A1 | 6/2003 | Li et al. |
| 2003/0124055 A1 | 7/2003 | Li et al. |
| 2003/0124143 A1 | 7/2003 | Phalipon |
| 2003/0130170 A1 | 7/2003 | Li et al. |
| 2003/0130178 A1 | 7/2003 | Li et al. |
| 2003/0130341 A1 | 7/2003 | Li et al. |
| 2003/0134793 A1 | 7/2003 | Li et al. |
| 2003/0147807 A1 | 8/2003 | Li et al. |
| 2003/0166507 A1 | 9/2003 | Li et al. |
| 2003/0170201 A1 | 9/2003 | Kataoka et al. |
| 2003/0181359 A1 | 9/2003 | Bebbington et al. |
| 2003/0195152 A1 | 10/2003 | Suarato et al. |
| 2003/0211973 A1 | 11/2003 | Bhatt et al. |
| 2003/0216289 A1 | 11/2003 | Bhatt et al. |
| 2003/0224971 A1 | 12/2003 | Kumar et al. |
| 2003/0232968 A1 | 12/2003 | Li et al. |
| 2004/0018960 A1 | 1/2004 | Li et al. |
| 2004/0043030 A1 | 3/2004 | Griffiths et al. |
| 2004/0047835 A1 | 3/2004 | Bianco |
| 2004/0121954 A1 | 6/2004 | Xu |
| 2004/0136911 A1 | 7/2004 | Uzgiris et al. |
| 2004/0151690 A1 | 8/2004 | Nakanishi et al. |
| 2004/0170563 A1 | 9/2004 | Meade |
| 2004/0198638 A1 | 10/2004 | Li et al. |
| 2005/0118718 A1 | 6/2005 | Bae et al. |
| 2005/0152842 A1 | 7/2005 | Li et al. |
| 2005/0187147 A1 | 8/2005 | Newman et al. |
| 2005/0214375 A1 | 9/2005 | Nakanishi et al. |
| 2005/0266067 A1 | 12/2005 | Sengupta et al. |
| 2005/0271585 A1 | 12/2005 | Uzgiris et al. |
| 2005/0276783 A1 | 12/2005 | Lledo et al. |
| 2006/0013800 A1 | 1/2006 | Le Buanec et al. |
| 2006/0046967 A1 | 3/2006 | Satyam |
| 2006/0067910 A1 | 3/2006 | Kitagawa et al. |
| 2006/0088592 A1 | 4/2006 | Choi et al. |
| 2006/0111273 A1 | 5/2006 | Li et al. |
| 2006/0135404 A1 | 6/2006 | Li et al. |
| 2006/0205674 A2 | 9/2006 | Satyam |
| 2007/0128118 A1 | 6/2007 | Yu et al. |
| 2007/0148125 A1 | 6/2007 | Kataoka et al. |
| 2008/0051603 A1 | 2/2008 | McKennon et al. |
| 2008/0181852 A1 | 7/2008 | Yu et al. |
| 2008/0253969 A1 | 10/2008 | Yu et al. |
| 2008/0279777 A1 | 11/2008 | Van et al. |
| 2008/0279778 A1 | 11/2008 | Van et al. |
| 2008/0279782 A1 | 11/2008 | Van et al. |
| 2009/0226393 A1 | 9/2009 | Wang et al. |
| 2010/0093935 A1 | 4/2010 | Van et al. |
| 2011/0144315 A1 | 6/2011 | Wang et al. |
| 2011/0224148 A1 | 9/2011 | Ahmadian et al. |
| 2012/0052015 A1 | 3/2012 | Yu et al. |

FOREIGN PATENT DOCUMENTS

| | | |
|---|---|---|
| EP | 0693288 | 1/1996 |
| EP | 0517740 | 10/1996 |
| EP | 0526503 | 6/1997 |
| EP | 0832851 | 4/1998 |
| EP | 1031354 | 8/2000 |
| EP | 1279405 A | 1/2003 |
| EP | 1514560 A | 3/2005 |
| EP | 1580216 A | 9/2005 |
| EP | 1695991 A | 8/2006 |
| JP | 5-178983 | 7/1993 |
| JP | 2001288097 | 10/2001 |
| WO | WO 97/33552 | 9/1997 |
| WO | WO 99/43311 | 9/1999 |
| WO | WO 99/49901 | 10/1999 |
| WO | WO 00/63409 | 10/2000 |
| WO | WO 01/26693 A | 4/2001 |
| WO | WO 01/70275 | 9/2001 |
| WO | WO 02/26241 | 4/2002 |
| WO | WO 02/087497 A | 11/2002 |
| WO | WO 02/087498 | 11/2002 |
| WO | WO 03/017923 | 3/2003 |
| WO | WO 03/041642 A2 | 5/2003 |
| WO | WO 03/055935 | 7/2003 |
| WO | WO 2004/039869 | 5/2004 |
| WO | WO 2004/099375 | 11/2004 |
| WO | WO 2005/056641 | 6/2005 |
| WO | WO 2005/079861 | 9/2005 |
| WO | WO 2005/110013 | 11/2005 |
| WO | WO 2005/121181 | 12/2005 |
| WO | WO 2006/041613 A | 4/2006 |
| WO | WO 2006/042146 A | 4/2006 |
| WO | WO 2006/060797 A | 6/2006 |
| WO | WO 2007/067417 A | 7/2007 |
| WO | WO 2008/094834 A | 8/2008 |
| WO | WO 2008/141107 | 11/2008 |
| WO | WO 2008/141110 A | 11/2008 |
| WO | WO 2008141111 A | 11/2008 |
| WO | WO 2009/111271 | 9/2009 |
| WO | WO 2010/029760 | 3/2010 |
| WO | WO 2010/045370 | 4/2010 |
| WO | WO 2011/075483 | 6/2011 |
| WO | WO 2011/112733 | 9/2011 |
| WO | WO 2012/027204 | 3/2012 |

OTHER PUBLICATIONS

Bourke et al., "Polymers derived from the amino acid L-tyrosine: polycarbonates, polyarylates and copolymers with poly(ethylene glycol)," *Adv. Drug Del. Rev.*, (2003) 55: 447-466.

Brannon-Peppas et al., "Nanoparticle and targeted systems for cancer therapy," *Adv. Drug Del. Rev.*, (2004) 56: 1649-1659.

Bulte et al., "Magnetic resonance microscopy and histology of the CNS." *Trends in Biotechnology*, (2002) 20: S24-S28.

Bundgaard et al., *Design of Prodrugs*, Elsevier Science Publishing Company, New York, NY, (1985) [Table of Contents Only].

Caravan et al., "Gadolinium(III) Chelates as MRI Contrast Agents: Structure, Dynamics, and Applications," *Chem. Rev.*, (1999) 99: 2293-2352.

Constantinides et al., "Formulation Development and Antitumor Activity of a Filter-Sterilizable Emulsion of Paclitaxel," *Pharmaceutical Research*, (2000) 17: 175-182.

Damascelli et al., "Intraarterial chemotherapy with polyoxyethylated castor oil free paclitaxel, incorporated in albumin nanoparticles (ABI-007): Phase II study of patients with squamous cell carcinoma of the head and neck and anal canal: preliminary evidence of clinical activity," *Cancer*. (2001) 92: 2592-2602.

De Winne, et al., "Dendritic Poly-[N-(2-Hydroxyethyl)-L-Glutamine]as Potential Drug Carrier," *Journal of Bioactive and Compatible Polymers*, (2004) 19:367-382.

Winne, et al., "Succinoylated Poly[N-(2-Hydroxyethyl)-L-Glutamine] Derivatives for Drug Delivery," *Journal of Bioactive and Compatible Polymers*, (2004) 19:439-452.

De Winne, et al., "Synthesis and in vitro evaluation of macromolecular antitumour derivatives based on phenylenediamine mustard," *Eur. J. Pharm Sci.*, (2005) 24(2-3):159-68.

Dekie, et al., "Poly-L-glutamic acid derivatives as vectors for gene therapy," *J. Control Release*, (2000) 65(1-2):187-202.

Dubruel, et al., "Poly-L-glutamic Acid Derivatives as Multifunctional Vecotrs for Gene Delivery.Part A. Dynthesis and Physicochemical Evaluation," *Biomacromolecules*, (2003) 4(5):1168-1176.

Dubruel, et al., "Poly-L-glutamic Acid Derivatives as Multifunctional Vecotrs for Gene Delivery.Part B. Biological Evaluation," *Biomacromolecules*, (2003) 4(5):1177-1183.

Duncan, "The Dawning era of polymer therapeutics," *Nature Reviews Drug Discovery* (2003) 2: 347-360.

Feng, et al., "Antitumor activity of nexil in preclinical animal tumor models," *Nitto Denko Technical Corporation, Abstract #2319 presented at 99th AACR Annual Meeting conference* Apr. 12-16, 2008 in San Diego, CA.

Fingl et al., "The Pharmacological Basis of Therapeutics," Macmillan Publishing Co., New York, NY, (1975), Chapter 1, p. 1.

Greene et al., *Protective Groups in Organic Synthesis*, 3rd Ed., John Wiley & Sons, New York, NY, (1999), [Table of Contents Only].

Haag, et al., "Polymer Therapeutics: Concept and Application," *Angew. Chem. Int. Ed.*, (2006) 45: 1198-1215.

He, et al., "Evaluation of membranes of copolypeptide of γ-benzyl L-glutamate and L-glutamic acid for the permeability of anticancer drugs," *Journal of Membrane Science*, (1997) 130:17-21.

Heller et al., "Poly(ortho esters): synthesis, characterization, properties and uses," *Adv. Drug Del. Rev.* (2002) 54: 1015-1039.

Helmus, et al., "Surface analysis of a series of copolymers of L-glutamic acid and L-leucine," *Journal of Colloid and Interface Science*, (1982) 89(2):567-570.

Higuchi et al., "Pro-drugs as Novel Delivery Systems," *A.C.S. Symposium Series, American Chemical Society* (1975) vol. 14, [Table of Contents Only].

Hoes, et al., "Optimization of macromolecular prodrugs of the antitumor antibiotic adriamycin," *J. of Controlled Release*, (1985) 2:205-213.

Hornback, et al., "Organic Chemistry" (1998): 50.

Hoste, et al., "New derivatives of polyglutamic acid as drug carrier systems," *J. of Controlled Release*, (2000) 64:53-61.

Huh, et al., "Structure and ion permeability of poly(L-glutamic acid) membranes prepared under a high electric field," *Sen'i Gakkaishi*, (1996) 52:148-151.

Ibrahim et al., "Phase I and pharmacokinetic study of ABI-007, a Cremophor-free, protein-stabilized, nanoparticle formulation of paclitaxel," *Clin Cancer Res.* 8 (2002): 1038-44.

International Search Report and the Written Opinion dated Apr. 23, 2009 for PCT Application No. PCT/US2008/063126 filed May 8, 2008.

International Search Report and the Written Opinion dated Apr. 24, 2009 for PCT Application No. PCT/US2008/063128 filed May 8, 2008.

International Search Report and the Written Opinion dated Jul. 29, 2009 for PCT Application No. PCT/US2009/035335 filed Feb. 26, 2009.

International Search Report and the Written Opinion dated Mar. 19, 2009 for PCT Application No. PCT/US2008/052094 filed Jan. 25, 2008.

International Search Report and the Written Opinion dated Mar. 27, 2009 for PCT Application No. PCT/US2008/059677 filed Apr. 8, 2008.

International Search Report and the Written Opinion dated Mar. 9, 2009 for PCT Application No. PCT/US2008/063114 filed May 8, 2008.

International Search Report and the Written Opinion dated May 4, 2007 for PCT Application No. PCT/US2006/045915 filed on Dec. 1, 2006.

Joshi, Microparticulates for ophthalmic drug delivery, *J. Ocul. Pharmacol*, (1994) 10: 29-45.

Kelner, et al., "Tailor-made polymers for local drug delivery: release of macromolecular model drugs from biodegradable hydrogels based on poly(ethylene oxide)," *J.Control Release*, (2005) 101:13-20.

Kumar N et al., "Polyanhydrides: an overview," *Adv. Drug Del. Rev.* 54 (2002): 889-910.

Lauffer et al., "Preparation and Water Relaxation Properties of Proteins Labeled with Paramagnetic Metal Chelates," *Magn. Reson. Imaging*, (1985) 3: 11-16.

Lazar et al. "Biological effect of basic polyglutamic acid derivatives," *Acta Physiologica Academiae Scientiarum Hungaricae*, (1972) 41: 113-23.

Lazar et al., "Experimental production of hemorrhagic lesions in the rat adrenal, liver, and lung by basic polyglutamic acid derivative," *Research in Experimental Medicine*, (1972) 159: 58-64.

Li et al., "Complete Regression of Well-established tumors using a novel water-soluble poly(L-glutamic acid)-paclitaxel conjugate," *Cancer Research*, (1998) 58: 2404-09.

Li, Chun, "Poly(L-glutamic acid)-anticancer drug conjugates," *Adv. Drug Del. Rev.*, (2002) 54: 695-713.

Line, et al., "Targeting tumor angiogenesis: comparison of peptide and polymer-peptide conjugates," *Journal of Nuclear Medicine*, (2005) 46:1552-1560.

Lonikar, et al., "Block copolymers of polysaccharides and polyamino acid," *Polymer Preprints*, (1990) 31(1):640-641.

Lu et al. "Poly(L-glutamic acid) Gd(III)-DOTA Conjugate with a Degradable Spacer for Magnetic Resonance Imaging," *Bioconjugate Chem.* (2003) 14: 715-719.

Matsumura et al. "Phase I clinical trial and pharmacokinetic evaluation of NK911, a micelle-encapsulated doxorubicin," *British Journal of Cancer*, (2004) 91: 1775-1781.

Mayer et al., "Efficacy of a novel hydrogel formulation in human volunteers," *Ophthalmologica*, (1996) 210: 101-103.

Mita, et al., "Phase I study of paclitaxel poliguмex administered weekly for patients with advanced aolid malignancies," *Cancer Chemother Pharmacol*, (2009) 64:287-295.

Mitra, et al., "Polymeric conjugates of mono- and bi-cyclic alphaVbeta3 binding peptides for tumor targeting," *Journal of Controlled Release*, (2006) 114:175-183.

Monks et al., "Feasibility of a high-flux anticancer drug screen using a diverse panel of cultured human tumor cell lines," *J. Natl. Cancer Inst.*, (1991) 83: 757-766.

Mordenti, "Intraocular pharmacokinetics and safety of a humanized monoclonal antibody in rabbits after intravitreal administration of a solution or a PLGA microsphere formulation," *Toxicol. Sci.*, (1999) 52: 101-106.

Nagata Y. et al., "Copper Ion Complex Formation of a Dicarboxylic Acid-Containing Polypeptide," *Polymer Journal, Society of Polymer Science*, Tokyo, JP, (1994) 26: 43-48.

Panyam et al. "Biodegradable nanoparticles for drug and gene delivery to cells and tissue," *Adv. Drug Del. Rev.*, (2003) 55: 329-347.

Pechar, et al., "Poly(ethylene glycol) Multiblock Copolymer as a Carrier of Anti-Cancer Drug Doxorubicin," *Bioconjugate Chem.*, (2000) 11(2):131-139.

Pemawansa, et al., "Macromolecular complexes of helical sodium poly (alpha,L-glutamate) (PGNA) with copolymers (block and random) of ethylene oxide (EO) and propylene oxide (PO)," Polymer Preprints, (2000) 41(1): 965-966.

Remington, *Remington's Pharmaceutical Sciences*, 18th Ed., Mack Publishing Co., Easton, PA (1990) [Table of Contents Only].

Rigbi, et al., "Inhibition of trypsin by copolymers of glutamic acid and other amino acids," *Biochemistry*, (1964) 3(5):629-636.

Roche, "Bioreversible Carriers in Drug Design: Theory and Application," *Pergamon Press* (1987) pp. 14-21.

Rowland et al., "Suppression of tumour growth in mice by a drug antibody conjugate using a novel approach to linkage," *Nature*, (1975) 256: 487-488.

Scagliotti, et al., "Phase II Study of Premetrexed with and Without folic acid and vitamin B12 as front-line therapy in malignant pleural meothioma" *J. Clin. Oncol.* (2003) 21:8, pp. 1556-1561.

Sengupta et al. "Temporal targeting of tumour cells and neovasculature with a nanoscale delivery system," *Nature* (2005) 438: 568-572.

Shedden et al., "Efficacy and tolerability of timolol maleate ophthalmic gel-forming solution versus timolol ophthalmic solution in adults with open-angle glaucoma or ocular hypertension: a six-month, double-masked, multicenter study," *Clin. Ther*, (2001) 23: 440-450.

Sidman et al., "Biodegradable, implantable sustained release systems based on glutamic acid copolymers," *Journal of Membrane Science*, (1980) 7: 277-291.

Sidman et al., "Controlled release of macromolecules and pharmaceuticals from synthetic polypeptides based on glutamic acid," *Biopolymers*, (1983) 22: 547-56.

Sirlin et al., "Gadolinium-DTPA-Dextran: A Macromolecular MR Blood Pool Contrast Agent," *Academic Radiology*, (2004) 11: 1361-1369.

Sparreboom et al., "Cremophor EL-mediated Alteration of Paclitaxel Distribution in Human Blood: Clinical Pharmacokinetic Implications," *Cancer Research*, (1999) 59: 1454-1457.

Srivastava, et al., "Synthetic substituted enzymes: Part III Glutamic acid copolymers with lysozyme-like activity," *Experientia*, (1970) 26:11-12.

Tadros et al., "Z-protected glutamic acid-based biodegradable thermoplastic and thermosetting polyesters: synthesis and characterization," *Journal of Applied Polymer Science* (1999) 73: 869-879.

Tansey, et al., "Synthesis and characterization of branched poly(L-glutamic acid) as a biodegradable drug carrier", (2004), *J. Controlled Release*, 94 pp. 39-51.

Thunemann, et al., "Maghemite nanoparticles protectively coated with poly(ethylene imine) and Poly (ethylene oxide)-block-poly(glutamic acid)," *American Chemical Society*, (2006) 22(5):2351-2357.

Uchino, et al., "Cisplatin-incorporating polymeric micelles (NC-6004) can reduce nephrotoxicity and neurotoxicity of cisplatin in rats," *British Journal of Cancer*, (2005) 93(6):678-687.

Uhrich et al., "Polymeric Systems for Controlled Drug Release," *Chem. Rev.* (1999) 99: 3181-3198.

Vega, et al., "Targeting doxorubicin to epidermal growth factor receptors by site specific conjugation of C225 to poly(L-glutamic acid) through a polyethylene glycol spacer," *Pharm. Res.*, (2003) 20:826-832.

Wang, et al., "Pharmacokinetics and tissue distribution of a novel macromolecular formulation of paclitaxel in nu/nu mice bearing NCI-460 lung cancer xenografts," *Nitto Denko Technical Corporation Abstract #2917 presented at 100th AACR Annual Meeting conference* Apr. 18-22, 2009 in Denver, CO.

Wang, et al., "Pharmacokinetics and tissue distribution of nexil, a novel macromolecular formulation of paclitaxel, in nu/nu mice bearing nci-460 lung cancer xenografts," *Nitto Denko Technical Corporation Abstract #5738 presented at 99th AACR Annual Meeting conference* Apr. 12-16, 2008 in San Diego, CA.

Wani et al., "Plant antitumor agents. VI. The isolation and structure of taxol, a novel antileukemic and antitumor agent from *Taxus brevifolia*," *J. Am. Chem. Soc.*, (1971) 93 : 2325-27.

Weinmann et al., "Tissue-specific MR contrast agents," *Eur. J. Radiology*, (2003) 46: 33-44.

Wen et al., "Synthesis and Characterization of Poly(L-glutamic acid) Gadolinium Chelate: A New Biodegradable MRI Contrast Agent," *Bioconjugate Chem.*, (2004) 15: 1408-1415.

Williams, et al., "Biometric Diels-Alder Cyclizations for the Construction of the Brevianamide, Paraherquamide, Sclerotamide and VM55599 Ring Systems," *Journal of the America Chemical Society*, (1998) 120:1090-1091.

Ye et al., "Poly($\gamma$, L-glutamic acid)-cisplatin conjugate effectively inhibits human breast tumor xenografted in nude mice," *Biomaterials* (2006) 27: 5958-5965.

Office Action issued on Oct. 27, 2011 for U.S. Appl. No. 12/117,601, filed May 8, 2008.

Office Action issued on Nov. 4, 2011 for European Patent Application No. 08 795 840.1, filed May 8, 2008.

Office Action issued on Jun. 1, 2011 for Chinese Patent Application No. 200880015368.8, filed May 8, 2008.

PGA-G-paclitaxel conjugate
R = —O-paclitaxel

For Example paclitaxel

Formulation

COMPOSITIONS THAT INCLUDE A HYDROPHOBIC COMPOUND AND A POLYAMINO ACID CONJUGATE

This application is a continuation of U.S. application Ser. No. 12/117,601, now U.S. Pat. No. 8,197,828, entitled "COMPOSITIONS THAT INCLUDE A HYDROPHOBIC COMPOUND AND A POLYAMINO ACID CONJUGATE," filed on May 8, 2008 which claims priority to U.S. Provisional Application No. 60/916,903, entitled "COMPOSITIONS THAT INCLUDE A HYDROPHOBIC COMPOUND AND A POLYAMINO ACID CONJUGATE," filed on May 9, 2007; both of which are incorporated herein by reference in their entireties.

BACKGROUND OF THE INVENTION

1. Field of the Invention

Generally disclosed herein are compositions that include a hydrophobic compound and a polyamino acid conjugate. The compositions described herein are useful for a variety of drug, biomolecule, and imaging agent delivery applications. Also disclosed are methods of using the compositions described herein to treat, diagnose, and/or image a subject.

2. Description of the Related Art

A variety of systems have been used for the delivery of drugs, biomolecules, and imaging agents. For example, such systems include capsules, liposomes, microparticles, nanoparticles, and polymers.

A variety of polyester-based biodegradable systems have been characterized and studied. Polylactic acid (PLA), polyglycolic acid and their copolymers polylactic-co-glycolic acid (PLGA) are some of the better characterized biomaterials with regard to design and performance for drug-delivery applications. See Uhrich, K. E., Cannizzaro, S. M., Langer, R. S., and Shakeshelf, K. M.; "Polymeric Systems for Controlled Drug Release," Chem. Rev. 1999, 99, 3181-3198 and Panyam J, Labhasetwar V. "Biodegradable nanoparticles for drug and gene delivery to cells and tissue," Adv. Drug. Deliv. Rev. 2003, 55, 329-47. Also, 2-hydroxypropyl methacrylate (HPMA) has been widely used to create a polymer for drug-delivery applications. Biodegradable systems based on poly-orthoesters have also been investigated. See Heller, J.; Barr, J.; Ng, S. Y.; Abdellauoi, K. S, and Gurny, R. "Poly(ortho esters): synthesis, characterization, properties and uses." Adv. Drug Del. Rev. 2002, 54, 1015-1039. Polyanhydride systems have also been investigated. Such polyanhydrides are typically biocompatible and may degrade in vivo into relatively non-toxic compounds that are eliminated from the body as metabolites. See Kumar, N.; Langer, R. S, and Domb, A. J. "Polyanhydrides: an overview," Adv. Drug Del. Rev. 2002, 54, 889-91.

Amino acid-based polymers have also been considered as a potential source of new biomaterials. Poly-amino acids having good biocompatibility have been investigated to deliver low molecular-weight compounds. A relatively small number of polyglutamic acids and copolymers have been identified as candidate materials for drug delivery. See Bourke, S. L. and Kohn, J. "Polymers derived from the amino acid L-tyrosine: polycarbonates, polyarylates and copolymers with poly(ethylene glycol)." Adv. Drug Del. Rev., 2003, 55, 447-466.

Administered hydrophobic anticancer drugs, therapeutic proteins, and polypeptides often suffer from poor bio-availability. Such poor bio-availability may be due to incompatibility of bi-phasic solutions of hydrophobic drugs and aqueous solutions and/or rapid removal of these molecules from blood circulation by enzymatic degradation. One technique for increasing the efficacy of administered proteins and other small molecule agents entails conjugating the administered agent with a polymer, such as a polyethylene glycol ("PEG") molecule, that can provide protection from enzymatic degradation in vivo. Such "PEGylation" often improves the circulation time and, hence, bio-availability of an administered agent.

PEG has shortcomings in certain respects, however. For example, because PEG is a linear polymer, the steric protection afforded by PEG is limited, as compared to branched polymers. Another shortcoming of PEG is that it is generally amenable to derivatization at its two terminals. This limits the number of other functional molecules (e.g. those helpful for protein or drug delivery to specific tissues) that can be conjugated to PEG.

Polyglutamic acid (PGA) is another polymer of choice for solubilizing hydrophobic anticancer drugs. Many anti-cancer drugs conjugated to PGA have been reported. See Chun Li. "Poly(L-glutamic acid)-anticancer drug conjugates." Adv. Drug Del. Rev., 2002, 54, 695-713. However, none are currently FDA-approved.

Paclitaxel, extracted from the bark of the Pacific Yew tree, is a FDA-approved drug for the treatment of ovarian cancer and breast cancer. Wani et al. "Plant antitumor agents. VI. The isolation and structure of taxol, a novel antileukemic and antitumor agent from *Taxus brevifolia*," J. Am. Chem. Soc. 1971, 93, 2325-7. However, like other anti-cancer drugs, paclitaxel suffers from poor bio-availability due to its hydrophobicity and insolubility in aqueous solution. One way to solubilize paclitaxel is to formulate it in a mixture of Cremophor-EL and dehydrated ethanol (1:1, v/v). Sparreboom et al. "Cremophor EL-mediated Alteration of Paclitaxel Distribution in Human Blood: Clinical Pharmacokinetic Implications," Cancer Research, 1999, 59, 1454-1457. This formulation is currently commercialized as Taxol® (Bristol-Myers Squibb). Another method of solubilizing paclitaxel is by emulsification using high-shear homogenization. Constantinides et al. "Formulation Development and Antitumor Activity of a Filter-Sterilizable Emulsion of Paclitaxel," Pharmaceutical Research 2000, 17, 175-182. Recently, polymer-paclitaxel conjugates have been advanced in several clinical trials. Ruth Duncan, "The Dawning era of polymer therapeutics," Nature Reviews Drug Discovery 2003, 2, 347-360. More recently, paclitaxel has been formulated into nanoparticles with human albumin protein and has been used in clinical studies. Damascelli et al., "Intraarterial chemotherapy with polyoxyethylated castor oil free paclitaxel, incorporated in albumin nanoparticles (ABI-007): Phase II study of patients with squamous cell carcinoma of the head and neck and anal canal: preliminary evidence of clinical activity." Cancer, 2001, 92, 2592-602, and Ibrahim et al. "Phase I and pharmacokinetic study of ABI-007, a Cremophor-free, protein-stabilized, nanoparticle formulation of paclitaxel," Clin. Cancer Res. 2002, 8, 1038-44. This formulation is currently commercialized as Abraxane® (American Pharmaceutical Partners, Inc.).

Magnetic resonance imaging (MRI) is an important tool in diagnosis and staging of disease because it is non-invasive and non-irradiating. See Bulte et al. "Magnetic resonance microscopy and histology of the CNS," Trends in Biotechnology, 2002, 20, S24-S28. Although images of tissues can be obtained, MRI with contrast agents significantly improves its resolution. However, paramagnetic metal ions suitable for MRI contrast agents are often toxic. One of the methods to reduce toxicity is to chelate these metal ions with polydentate molecules such as diethylenetriamine pentaacetate molecules (DTPA). Gd-DTPA was approved by FDA in 1988 for clinical uses, and it is currently commercialized as Magnevist®. Other Gd-chelates were approved by FDA and commercialized, and many others are under development. See Caravan et al. "Gadolinium(III) Chelates as MRI Contrast Agents: Structure, Dynamics, and Applications," Chem. Rev. 1999, 99, 2293-2352.

However, Gd-DTPA is not ideal for targeting tumor tissues because it lacks specificity. When Gd-DTPA is administered via IV injection, it spontaneously and rapidly diffuses into extravascular space of the tissues. Thus, large amounts of contrast agents are usually required to produce reasonable contrast images. In addition, it is quickly eliminated via kidney filtration. To avoid the diffusion and the filtration, macromolecular MRI contrast agents have been developed. See Caravan et al. "Gadolinium(III) Chelates as MRI Contrast Agents: Structure, Dynamics, and Applications," Chem. Rev. 1999, 99, 2293-2352. These macromolecular-MRI contrast agents include protein-MRI chelates, polysaccharide-MRI chelates, and polymer-MRI chelates. See Lauffer et al. "Preparation and Water Relaxation Properties of Proteins Labeled with Paramagnetic Metal Chelates," Magn. Reson. Imaging 1985, 3, 11-16; Sirlin et al. "Gadolinium-DTPA-Dextran: A Macromolecular MR Blood Pool Contrast Agent," Acad. Radiol. 2004, 11, 1361-1369; Lu et al. "Poly (L-glutamic acid) Gd(III)-DOTA Conjugate with a Degradable Spacer for Magnetic Resonance Imaging," Bioconjugate Chem. 2003, 14, 715-719; and Wen et al. "Synthesis and Characterization of Poly(L-glutamic acid) Gadolinium Chelate: A New Biodegradable MRI Contrast Agent," Bioconjugate Chem. 2004, 15, 1408-1415.

Recently, tissue-specific MRI contrast agents have been developed. See Weinmann et al. "Tissue-specific MR contrast agents." Eur. J. Radiol. 2003, 46, 33-44. However, tumor-specific MRI contrast agents have not been reported in clinical applications. Nano-size particles have been reported to target tumor-tissues via an enhanced permeation and retention (EPR) effect. See Brannon-Peppas et al. "Nanoparticle and targeted systems for cancer therapy." ADDR, 2004, 56, 1649-1659).

SUMMARY OF THE INVENTION

Relatively hydrophobic imaging agents and drugs (such as certain hydrophobic anti-cancer drugs, therapeutic proteins and polypeptides) often suffer from poor bioavailability. It is believed that this problem is due, at least in part, to the poor solubility of these imaging agents and drugs in aqueous systems. Certain enzymatically degradable drugs also suffer from poor bioavailability because they are degraded relatively rapidly in the circulatory system, resulting in rapid elimination from the body.

The inventors have discovered novel compositions that include a polymer conjugate, a first hydrophobic drug, and a second hydrophobic drug. The polymer conjugates of the compositions described herein are capable of conjugating to a number of agents, such as imaging agents, targeting agents, stabilizing agents and/or drugs. In some embodiments, the polymers and the resulting conjugates preferentially accumulate in certain tissues (e.g., tumor tissues) and/or certain receptors, and thus are useful for delivering drugs (e.g., anti-cancer drugs) and/or imaging agents to specific parts of the body (e.g., tumors). In some embodiments, the polymers described herein and the resulting conjugates can form nanoparticles that effectively solubilize the drug in an aqueous system by dispersing it at a molecular level, thus increasing the functionality and/or bioavailability of the drug.

In some embodiments, the polymer conjugate can include a polymeric matrix that non-covalently holds the first hydrophobic drug, effectively encapsulating or partially encapsulating the first hydrophobic drug within the polymeric matrix. In an embodiment, a group that can include a second hydrophobic drug can be attached or conjugated to the polymer. The structures of the first and second hydrophobic drugs may be different, or alternatively, the structures of the first and second hydrophobic drugs may be the same.

An embodiment described herein relates to a composition that can include a first hydrophobic drug, a second hydrophobic drug and a polymer conjugate, wherein the polymer conjugate comprises a polymeric matrix that non-covalently encapsulates or partially encapsulates at least a portion of the first hydrophobic drug therein; the polymer conjugate comprises a recurring unit of the formula (I), described below; wherein n can be 1 or 2; each $A^1$ can be independently oxygen or $NR^5$, where $R^5$ can be hydrogen or $C_{1-4}$ alkyl; and at least one of $R^1$ and $R^2$ can be a group that comprises the second hydrophobic drug.

In some embodiments, if only one of $R^1$ and $R^2$ is the group that comprises the second hydrophobic drug, the other one of $R^1$ and $R^2$ can be selected from hydrogen, a $C_{1-10}$ alkyl group, a $C_{6-20}$ aryl group, an ammonium group, an alkali metal, a polydentate ligand, a polydentate ligand precursor with protected oxygen atoms, a group that comprises a targeting agent, a group that comprises an optical imaging agent, a group that comprises a magnetic resonance imaging agent, and a group that comprises a stabilizing agent.

Another embodiment described herein relates to a method of making the composition described herein comprising the steps of at least partially dissolving the polymer conjugate in a solvent, and intermixing the first hydrophobic drug with the at least partially dissolved polymer conjugate to form a mixture.

Yet still another embodiment described herein relates to a method of treating or ameliorating a disease or condition that can include administering an effective amount of the polymer conjugate described herein to a mammal in need thereof.

An embodiment described herein relates to a method of diagnosing a disease or condition that can include administering an effective amount of the polymer conjugate described herein to a mammal in need thereof.

Another embodiment described herein relates to a method of imaging a portion of tissue that can include contacting a portion of tissue with an effective amount of the polymer conjugate described herein.

These and other embodiments are described in greater detail below.

DETAILED DESCRIPTION OF THE PREFERRED EMBODIMENTS

Figure 1:
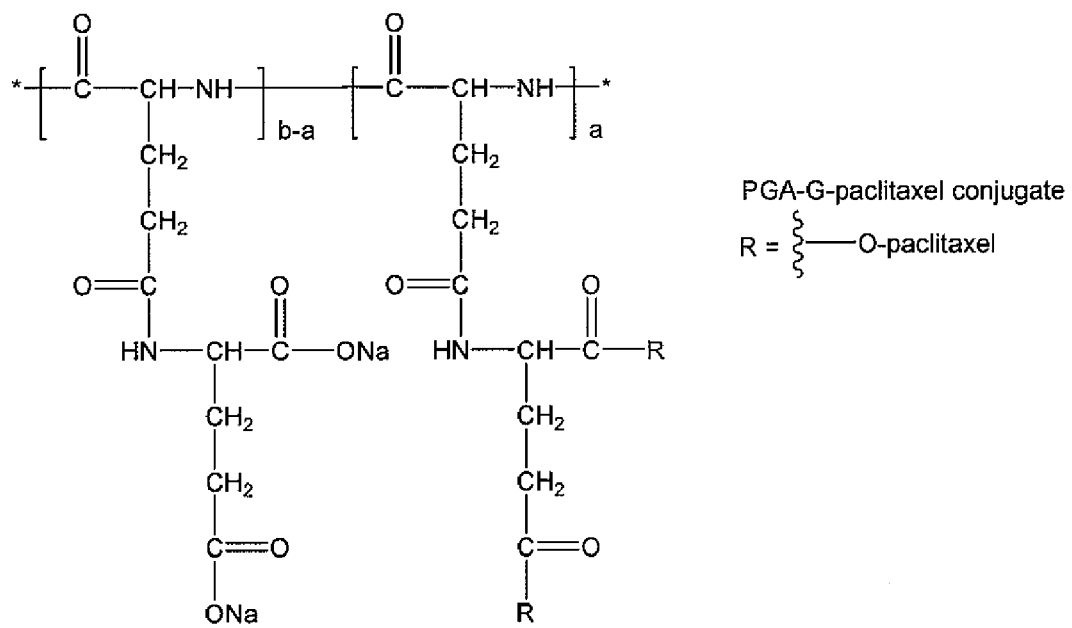
FIG. 1 shows a formulation scheme of encapsulating paclitaxel using a poly(γ-glutamyl-glutamine)-paclitaxel conjugate.
Figure 1:
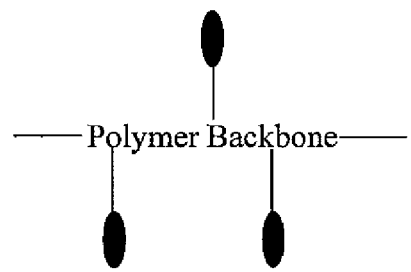
Figure 1:
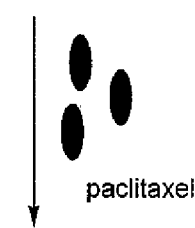
Figure 1:
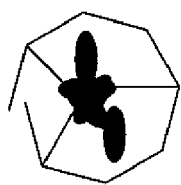

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "ester" is used herein in its ordinary sense, and thus includes a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

The term "amide" is used herein in its ordinary sense, and thus includes a chemical moiety with formula —$(R)_n$—C(O)NHR' or —$(R)_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be included in an amino acid or a peptide molecule attached to drug molecule as described herein, thereby forming a prodrug.

Any amine, hydroxy, or carboxyl side chain on the compounds disclosed herein can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

The alkyl group may be substituted or unsubstituted. When substituted, the substituent group(s) is (are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl (e.g., mono-, di- and tri-haloalkyl), haloalkoxy (e.g., mono-, di- and tri-haloalkoxy), trihalomethanesulfonyl, trihalomethanesulfonamido, and amino, including mono- and di-substituted amino groups, and the protected derivatives thereof. Wherever a substituent is described as being "optionally substituted" that substitutent may be substituted with one of the above substituents.

As used herein, "aryl" refers to a carbocyclic (all carbon) monocyclic or multicyclic aromatic ring system that has a fully delocalized pi-electron system. Examples of aryl groups include, but are not limited to, benzene, naphthalene and azulene. An aryl group of this invention may be substituted or unsubstituted. When substituted, hydrogen atoms are replaced by substituent group(s) that is (are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl (e.g., mono-, di- and tri-haloalkyl), haloalkoxy (e.g., mono-, di- and tri-haloalkoxy), trihalomethanesulfonyl, trihalomethanesulfonamido, and amino, including mono- and di-substituted amino groups, and the protected derivatives thereof, unless the substituent groups are otherwise indicated.

A "paramagnetic metal chelate" is a complex wherein a ligand is bound to a paramagnetic metal ion. Examples include, but are not limited to, 1,4,7,10-Tetraazacyclododecane-1,4,7,10-tetraacetic acid (DOTA)-Gd(III), DOTA-Yttrium-88, DOTA-Indium-111, diethylenetriaminepentaacetic acid (DTPA)-Gd(III), DTPA-yttrium-88, DTPA-Indium-111.

A "polydentate ligand" is a ligand that can bind itself through two or more points of attachment to a metal ion through, for example, coordinate covalent bonds. Examples of polydentate ligands include, but are not limited to, diethylenetriaminepentaacetic acid (DTPA), tetraazacyclododecane-1,4,7,10-tetraacetic acid (DOTA), (1,2-ethanediyldinitrilo)tetraacetate (EDTA), ethylenediamine, 2,2'-bipyridine (bipy), 1,10-phenanthroline (phen), 1,2-bis(diphenylphosphino)ethane (DPPE), 2,4-pentanedione (acac), and ethanedioate (ox).

A "polydentate ligand precursor with protected oxygen atoms" is a polydentate ligand comprising oxygen atoms, such as the single-bonded oxygen atoms of carboxyl groups, that are protected with suitable protecting groups. Suitable protecting groups include, but are not limited to, lower alkyls, benzyls, and silyl groups.

A "stabilizing agent" is a substituent that enhances bioavailability and/or prolongs the half-life of a carrier-drug conjugate in vivo by rendering it more resistant to hydrolytic enzymes and less immunogenic. An exemplary stabilizing agent is polyethylene glycol (PEG).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound described herein having one or more double bond(s) generating geometrical isomers that can be defined as E or Z each double bond may independently be E or Z a mixture thereof. Likewise, all tautomeric forms are also intended to be included.

An embodiment provides a composition that can include a first hydrophobic drug, a second hydrophobic drug and a polymer conjugate, wherein the polymer conjugate comprises a polymeric matrix that non-covalently entraps at least a portion of the first hydrophobic drug therein; the polymer conjugate can include a recurring unit of the formula (I):

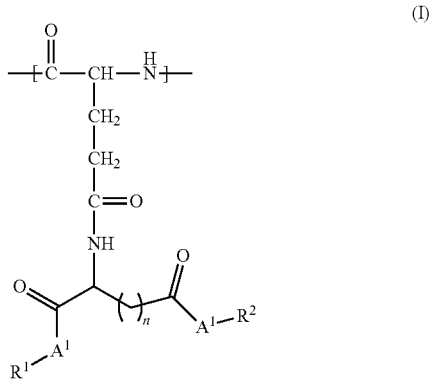

wherein n can be 1 or 2; each $A^1$ can be independently oxygen or $NR^5$, where $R^5$ can be hydrogen or $C_{1-4}$ alkyl; and at least one of $R^1$ and $R^2$ can be a group that can include the second hydrophobic drug. In some embodiments, n can be equal to 1. In other embodiments, n can be equal to 2.

In some embodiments, if only one of $R^1$ and $R^2$ is the group that comprises the second hydrophobic drug, the other one of $R^1$ and $R^2$ can be selected from hydrogen, a $C_{1-10}$ alkyl group, a $C_{6-20}$ aryl group, an ammonium group, an alkali metal, a polydentate ligand, a polydentate ligand precursor with protected oxygen atoms, a group that comprises a targeting agent, a group that comprises an optical imaging agent, a group that comprises a magnetic resonance imaging agent, and a group that comprises a stabilizing agent. The targeting agent, optical imaging agent, magnetic resonance imaging agent, and stabilizing agents may be referred to herein, in a general way, as "agents."

In some embodiments, the first hydrophobic drug has a chemical structure that is different from that of the second hydrophobic drug. In other embodiments, the first hydrophobic drug has a chemical structure that is the same as that of the second hydrophobic drug.

The compositions described herein can include a first hydrophobic drug and a second hydrophobic drug. The second hydrophobic drug can be covalently attached or conjugated to the polymer, while the first hydrophobic drug can be non-covalently encapsulated or partially encapsulated within the polymer matrix. In an embodiment, the release rates of the first hydrophobic drug and the second hydrophobic drug from the composition can vary as the composition degrades. The first hydrophobic drug releases at a first rate from the composition at a relative rate that is due, at least in part, to the manner in which it is non-covalently encapsulated within the polymer matrix. The second hydrophobic drug releases at a second rate from the composition because, at least in part, it is covalently bonded to the polymer conjugate. Thus, the first hydrophobic drug and the second hydrophobic drug have differing physical interactions with the polymer. As the polymer degrades, the first hydrophobic drug releases from the polymer in a different manner than the second hydrophobic drug releases from the polymer. In an embodiment, the first release rate is greater than the second release rate.

The compositions that can include a first hydrophobic drug, a second hydrophobic drug, and a polymer conjugate may be present in various forms. For example, the composition may be present in the form of particles, flakes, rods, fibers, films, foams, suspensions (in liquid or gas), a gel, a solid, and/or a liquid. The size and shape of these various forms is not limited. In an embodiment, the composition can be present in the form of particles. Particles of the composition may be any size or shape. In an embodiment, the particles can have a diameter of up to about 1000 microns. In an embodiment, the particles can have a diameter between about 0.1 microns and about 500 microns. In an embodiment, the particles can have a diameter between about 1 micron and about 100 microns. In an embodiment, the composition is present in the form of nanoparticles. In an embodiment, the nanoparticles can have a diameter between about 0.1 nanometers and about 500 nanometers. In an embodiment, the nanoparticles can have a diameter between about 1 nanometer and about 250 nanometers. In an embodiment, the nanoparticles can have a diameter between about 10 nanometers and about 100 nanometers.

The particle size may be adjusted to control the drug release rate of the composition in a particular environment, e.g., in vivo. Relatively larger particles of composition may have a longer lifetime than smaller particles. However, the rate at which the larger particles release the drug may be greater than smaller particles having a similar shape, due to the greater amount of surface area of the relatively larger particles. The degradation rate of the composition and the lifetime of the composition in a particular environment may be used to provide control over the amount of first hydrophobic drug and second hydrophobic drug that are released. Those skilled in the art, guided by the disclosure herein, can adjust the particle size to control the degradation rate of the composition and thus, further control the release rate of the first hydrophobic drug and the second hydrophobic drug.

In an embodiment, the size of the particle can provide for relatively long circulation time of the composition upon placement onto or administration to a subject. Relatively larger particles or nanoparticles having, for example, a diameter of about 100 nm, 200 nm, 500 nm, or larger degrade at a rate such that the composition has a relatively long half-life in the bloodstream after placement onto or administration to a subject. The longer circulation time of the composition, combined with varying release rates of the first hydrophobic drug and the second hydrophobic drug can provide improved accumulation of the drugs in a targeted tissue, such as a tumor tissue.

FIG. 1 is a non-limiting representation of an embodiment of a composition comprising a first hydrophobic drug, a second hydrophobic drug, and a polymer conjugate. FIG. 1 shows a formulation scheme, wherein the polymer conjugate (including the second hydrophobic drug) comprises a poly(γ-glutamyl-glutamine)-paclitaxel conjugate and the first hydrophobic drug comprises paclitaxel. As shown in FIG. 1, the second hydrophobic drug (in this example, paclitaxel), is covalently attached to the poly(γ-glutamyl-glutamine) at various branches along the polymer. This polymer conjugate may be dissolved or partially dissolved and then intermixed with a first hydrophobic drug (in this example, also paclitaxel) in a process described in detail below. The resulting composition or formulation is shown in FIG. 1, where the polymer conjugate maintains the paclitaxel covalently bonded thereto at various branches of the polymer, and also encapsulates or partially encapsulates the free paclitaxel within the polymer matrix.

In some embodiments, the polymer conjugate (comprising a recurring unit of formula (I)) can further include a recurring unit of the formula (II):

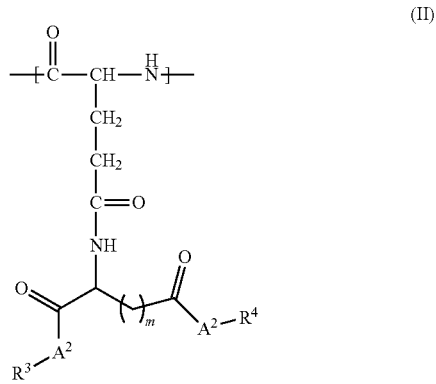

(II)

wherein m can be 1 or 2; each $A^2$ can be independently oxygen or $NR^6$, where $R^6$ can be hydrogen or a $C_{1-4}$ alkyl; and $R^3$ and $R^4$ can be each independently selected from hydrogen, ammonium, and an alkali metal. In some embodiments, m can be equal to 1. In other embodiments, m can be equal to 2.

The amount of first hydrophobic drug present in the composition can vary over a wide range. In an embodiment, the first hydrophobic drug can be present in an amount in the range of about 1% to about 50% (weight/weight) based on the mass ratio of the first hydrophobic drug to the combined weight of the first hydrophobic drug and the polymer conjugate (the weight of the first hydrophobic drug is accounted for in the polymer conjugate). In an embodiment, the first hydrophobic drug can be present in an amount in the range of about 1% to about 40% (weight/weight) based on the mass ratio of the first hydrophobic drug to the combined weight of the first hydrophobic drug and the polymer conjugate. In an embodiment, the first hydrophobic drug can be present in an amount in the range of about 1% to about 30% (weight/weight) based on the mass ratio of the first hydrophobic drug to the combined weight of the first hydrophobic drug and the polymer conjugate. In an embodiment, the first hydrophobic drug can be present in an amount in the range of about 1% to about 20% (weight/weight) based on the mass ratio of the first hydrophobic drug to the combined weight of the first hydrophobic drug and the polymer conjugate. In an embodiment, the first hydrophobic drug can be present in an amount in the range of about 1% to about 10% (weight/weight) based on the mass ratio of the first hydrophobic drug to the combined weight of the first hydrophobic drug and the polymer conjugate. In an embodiment, the first hydrophobic drug can be present in an amount in the range of about 5% to about 40% (weight/weight) based on the mass ratio of the first hydrophobic drug to the combined weight of the first hydrophobic drug and the polymer conjugate. In an embodiment, the first hydrophobic drug can be present in an amount in the range of about 10% to about 30% (weight/weight) based on the mass ratio of the first hydrophobic drug to the combined weight of the first hydrophobic drug and the polymer conjugate. In an embodiment, the first hydrophobic drug can be present in an amount in the range of about 20% to about 40% (weight/weight) based on the mass ratio of the first hydrophobic drug to the combined weight of the first hydrophobic drug and the polymer conjugate. In an embodiment, the first hydrophobic drug can be present in an amount in the range of about 30% to about 50% (weight/weight) based on the mass ratio of the first hydrophobic drug to the combined weight of the first hydrophobic drug and the polymer conjugate.

The amount of second hydrophobic drug present in the composition can also vary over a wide range. In an embodiment, the polymer conjugate can include an amount of the second hydrophobic drug in the range of about 1% to about 50% (weight/weight) based on the mass ratio of the second hydrophobic drug to the combined weight of the first hydrophobic drug and the polymer conjugate (the weight of the second hydrophobic drug is accounted for in the polymer conjugate). In an embodiment, the polymer conjugate can include an amount of the second hydrophobic drug in the range of about 1% to about 40% (weight/weight) based on the mass ratio of the second hydrophobic drug to the combined weight of the first hydrophobic drug and the polymer conjugate. In an embodiment, the polymer conjugate can include an amount of the second hydrophobic drug in the range of about 1% to about 30% (weight/weight) based on the mass ratio of the second hydrophobic drug to the combined weight of the first hydrophobic drug and the polymer conjugate. In an embodiment, the polymer conjugate can include an amount of the second hydrophobic drug in the range of about 1% to about 20% (weight/weight) based on the mass ratio of the second hydrophobic drug to the combined weight of the first hydrophobic drug and the polymer conjugate. In an embodiment, the polymer conjugate can include an amount of the second hydrophobic drug in the range of about 1% to about 10% (weight/weight) based on the mass ratio of the second hydrophobic drug to the combined weight of the first hydrophobic drug and the polymer conjugate. In an embodiment, the polymer conjugate can include an amount of the second hydrophobic drug in the range of about 5% to about 40% (weight/weight) based on the mass ratio of the second hydrophobic drug to the combined weight of the first hydrophobic drug and the polymer conjugate. In an embodiment, the polymer conjugate can include an amount of the second hydrophobic drug in the range of about 10% to about 30% (weight/weight) based on the mass ratio of the second hydrophobic drug to the combined weight of the first hydrophobic drug and the polymer conjugate. In an embodiment, the polymer conjugate can include an amount of the second hydrophobic drug in the range of about 20% to about 40% (weight/weight) based on the mass ratio of the second hydrophobic drug to the combined weight of the first hydrophobic drug and the polymer conjugate. In an embodiment, the polymer conjugate can include an amount of the second hydrophobic drug in the range of about 30% to about 50% (weight/weight) based on the mass ratio of the second hydrophobic drug to the combined weight of the first hydrophobic drug and the polymer conjugate.

The amount of agent(s), such as a targeting agent, an optical imaging agent, a magnetic resonance imaging agent, and a stabilizing agent, present in the polymer can vary over a wide range. Additionally, the amount of a ligand or a ligand precursor present in the polymer can vary over a wide range. In an embodiment, the polymer conjugate can include an amount of an agent(s), a ligand, and/or a ligand precursor in the range of about 0.1% to about 50% (weight/weight) based on the mass ratio of the agent(s), ligand, and/or ligand precursor to the polymer conjugate (the weight of the agent(s), ligand, and/or ligand precursor is accounted for, along with the weight of the second hydrophobic drug, in the polymer conjugate). In an embodiment, the polymer conjugate can include an amount of an agent(s), a ligand, and/or a ligand precursor in the range of about 1% to about 40% (weight/weight) based on the mass ratio of the agent(s), ligand, and/or ligand precursor to the polymer conjugate. In an embodiment, the polymer conjugate can include an amount of an agent(s), a ligand, and/or a ligand precursor in the range of about 1% to about 30% (weight/weight) based on the mass ratio of the agent(s), ligand, and/or ligand precursor to the polymer conjugate. In an embodiment, the polymer conjugate can include an amount of an agent(s), a ligand, and/or a ligand precursor in the range of about 1% to about 20% (weight/weight) based on the mass ratio of the agent(s), ligand, and/or ligand precursor to the polymer conjugate. In an embodiment, the polymer conjugate can include an amount of an agent(s), a ligand, and/or a ligand precursor in the range of about 1% to about 10% (weight/weight) based on the mass ratio of the agent(s), ligand, and/or ligand precursor to the polymer conjugate. In an embodiment, the polymer conjugate can include an amount of an agent(s), a ligand, and/or a ligand precursor in the range of about 5% to about 40% (weight/weight) based on the mass ratio of the agent(s), ligand, and/or ligand precursor to the polymer conjugate. In an embodiment, the polymer conjugate can include an amount of an agent(s), a ligand, and/or a ligand precursor in the range of about 10% to about 30% (weight/weight) based on the mass ratio of the agent(s), ligand, and/or ligand precursor to the polymer conjugate. In an embodiment, the polymer conjugate can include an amount of an agent(s), a ligand, and/or a ligand precursor in the range of about 20% to about 40% (weight/weight) based on the mass ratio of the agent(s), ligand, and/or ligand precursor to the polymer conjugate. In an embodiment, the polymer conjugate can include an amount of an agent(s), a ligand, and/or a ligand precursor in the range of about 30% to about 50% (weight/weight) based on the mass ratio of the agent(s), ligand, and/or ligand precursor to the polymer conjugate.

The polymer conjugate can contain one or more chiral carbon atoms. The chiral carbon (which may be indicated by an asterisk *) can have the rectus (right handed) or the sinister (left handed) configuration, and thus the recurring unit may be racemic, enantiomeric or enantiomerically enriched. The symbols "n" and "*" (designating a chiral carbon), as used elsewhere herein, have the same meaning as specified above, unless otherwise stated.

Polymers comprising a recurring unit of the formula (I) and a recurring unit of the formula (II) can be copolymers comprising two or more different recurring units of formulae (I) and (II). Further, polymers comprising a recurring unit of the formula (I) (including but not limited to polymers containing a recurring unit of the formula (II)) may be copolymers that comprise other recurring units that are not of the formula (I) and/or not of the formula (II). The number of recurring units of the formula (I) and recurring units of formula (II) in the polymer can each vary over a broad range, each independently may be in the range of from about 50 to about 5,000, such as from about 100 to about 2,000.

A broad variety of other recurring units may be included in the polymer conjugate with the recurring unit of formula (I) and, optionally, the recurring unit of formula (II). In some embodiments, the polymer conjugate further comprises a recurring unit of formula (III):

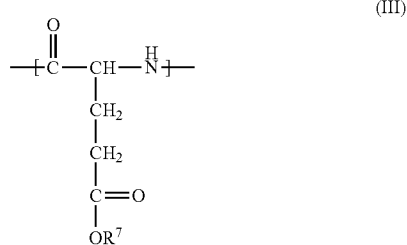

wherein $R^7$ can be hydrogen, ammonium, or an alkali metal. The number of recurring units of the formula (III) in the polymer can vary over a broad range as well. For example, the number of recurring units of the formula (III) may be in the range of from about 50 to about 5,000, such as from about 100 to about 2,000.

One or more of a group that comprises the first hydrophobic drug, a group that comprises the second hydrophobic drug, a group that comprises a targeting agent, a group that comprises an optical imaging agent, a group that comprises a magnetic resonance imaging agent, a group that comprises a polydentate ligand, a group that comprises a polydentate ligand precursor, or a group that comprises a stabilizing agent may be conjugated to the polymer in many different ways. In some embodiments, the aforementioned compounds can be directly attached to the polymer, e.g., to a recurring unit of formula (I). In one embodiment, one or more of a group that comprises the first hydrophobic drug, a group that comprises the second hydrophobic drug, a group that comprises a targeting agent, a group that comprises an optical imaging agent, a group that comprises a magnetic resonance imaging agent, a group that comprises a polydentate ligand, a group that comprises a polydentate ligand precursor, or a group that comprises a stabilizing agent can be directly attached to the polymer through an oxygen, a sulfur, a nitrogen and/or carbon atom of the agent or drug.

In other embodiments, one or more of a group that comprises the first hydrophobic drug, a group that comprises the second hydrophobic drug, a group that comprises a targeting agent, a group that comprises an optical imaging agent, a group that comprises a magnetic resonance imaging agent, a group that comprises a polydentate ligand, a group that comprises a polydentate ligand precursor, or a group that comprises a stabilizing agent can further include a linker group. In an embodiment, the group that comprises the first hydrophobic drug further can include a linker group. In an embodiment, the group that comprises the second hydrophobic drug further can include a linker group. In an embodiment, the group that comprises a targeting agent, the group that comprises an optical imaging agent, the group that comprises a magnetic resonance imaging agent, the group that comprises a polydentate ligand, a group that comprises the polydentate ligand precursor, and/or the group that comprises a stabilizing agent can include a linker group. A linker group is a group that attaches, for example, the agent (or the compound that comprises the agent) to the polymer. In an embodiment, one or more of the aforementioned compounds can be attached to the polymer, e.g., to a recurring unit of formula (I), through a linker group. The linker group may be relatively small. For instance, the linker group may comprise an amine, an amide, an ether, an ester, a hydroxyl group, a carbonyl group, or a thiol ether group. Alternatively, the linker group may be relatively large. For instance, the linker group may comprise an alkyl group, an ether group, an aryl group, an aryl($C_{1-6}$ alkyl) group (e.g., phenyl-$(CH_2)_{1-4}$—), a heteroaryl group, or a heteroaryl($C_{1-6}$ alkyl) group. In one embodiment, the linker can be —NH$(CH_2)_{1-4}$—NH—. In another embodiment, the linker can be —$(CH_2)_{1-4}$-aryl-NH—. The linker group can be attached to one or more of a group that comprises the first hydrophobic drug, a group that comprises the second hydrophobic drug, a group that comprises a targeting agent, a group that comprises an optical imaging agent, a group that comprises a magnetic resonance imaging agent, a group that comprises a polydentate ligand, a group that comprises a polydentate ligand precursor, or a group that comprises a stabilizing agent at any suitable position. For example, the linker group can be attached in place of a hydrogen at a carbon of one of the aforementioned compounds. The linker group can be added to the compounds using methods known to those skilled in the art.

Many different types of drugs may be used for the first hydrophobic drug. In an embodiment, the first hydrophobic drug can include an anticancer drug. In an embodiment, the anticancer drug can be selected from a taxane, a camptotheca, and an anthracycline. In an embodiment, the taxane can be selected from paclitaxel and docetaxel. In an embodiment, the taxane can be paclitaxel. In an embodiment, the camptotheca can be camptothecin. In an embodiment, the anthracycline can be doxorubicin. In another embodiment, the first drug can be hydrophilic, rather than hydrophobic. For example, hydrophilic drugs can be encapsulated or partially encapsulated within the polymeric matrix. Some examples of suitable hydrophilic drugs include, but not limited to, platinum drugs, such as cisplatin, carboplatin, and oxaliplatin.

Similarly, many different types of drugs may be used for the second hydrophobic drug. In an embodiment, the second hydrophobic drug can include an anticancer drug. In an embodiment, the anticancer drug can be selected from a taxane, a camptotheca, and an anthracycline. In an embodiment, the taxane can be selected from paclitaxel and docetaxel. In an embodiment, the taxane can be paclitaxel. In one embodiment wherein the second hydrophobic drug comprises paclitaxel, the paclitaxel can be attached or conjugated to the recurring unit of formula (I) at the oxygen atom attached to the C2'-carbon of the paclitaxel. In another embodiment, the paclitaxel can be attached or conjugated to the recurring unit of formula (I) at the oxygen atom attached to the C7-carbon of the paclitaxel. In an embodiment, the camptotheca can be camptothecin. In an embodiment, the anthracycline can be doxorubicin. In another embodiment, the second drug can be hydrophilic, rather than hydrophobic. For example, hydrophilic drugs can be conjugated to the polymers described herein. Some examples of suitable hydrophilic drugs include platinum drugs, such as those described herein.

The agent may comprise any type of active compound. In an embodiment, the agent may be an optical imaging agent. In an embodiment, the optical imaging agent can be one or more selected from an acridine dye, a coumarine dye, a rhodamine dye, a xanthene dye, a cyanine dye, and a pyrene dye. For instance, specific optical imaging agents may include Texas Red, Alexa Fluor® dye, BODIPY® dye, Fluorescein, Oregon Green® dye, and Rhodamine Green™ dye, which are commercially available or readily prepared by methods known to those skilled in the art.

In an embodiment, the agent may be a targeting agent. In an embodiment, the targeting agent can be one or more selected from an arginine-glycine-aspartate (RGD) peptide, fibronectin, folate, galactose, an apolipoprotein, insulin, transferrin, a fibroblast growth factor (FGF), an epidermal growth factor (EGF), and an antibody. In an embodiment, the targeting agent can interact with a receptor selected from $\alpha_v\beta_3$-integrin, folate, asialoglycoprotein, a low-density lipoprotein (LDL), an insulin receptor, a transferrin receptor, a fibroblast growth factor (FGF) receptor, an epidermal growth factor (EGF) receptor, and an antibody receptor. In an embodiment, the arginine-glycine-aspartate (RGD) peptide can be cyclic (fKRGD).

In an embodiment, the agent can be a magnetic resonance imaging agent. In an embodiment, the magnetic resonance imaging agent can include a paramagnetic metal compound. For example, the magnetic resonance imaging agent may comprise a Gd(III) compound. In an embodiment, the Gd(III) compound can be selected from:

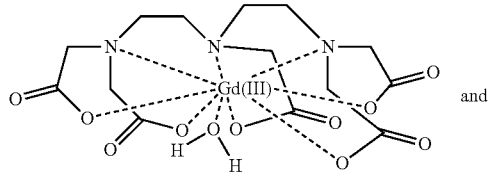 and

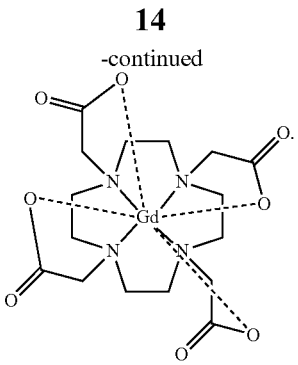

In an embodiment, the agent can include a stabilizing agent. In a preferred embodiment, the stabilizing agent can be polyethylene glycol.

In an embodiment, the polymer conjugate can include a polydentate ligand. In an embodiment, the polydentate ligand may be capable of reaction with a paramagnetic metal to form a magnetic resonance imaging agent. The polydentate ligand may comprise several carboxylic acid and/or carboxylate groups. In an embodiment, the polydentate ligand can be selected from:

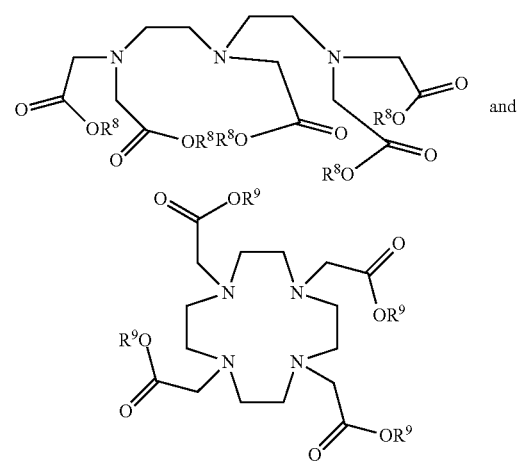

wherein each $R^8$ and each $R^9$ can be independently selected from hydrogen, ammonium, and an alkali metal.

In an embodiment, the polymer conjugate can include a polydentate ligand precursor. In such an embodiment, the oxygen atoms of the polydentate ligand may be protected by a suitable protecting group. Suitable protecting groups include, but are not limited to, lower alkyls, benzyls, and silyl groups. One example of a polydentate ligand precursor having protecting groups is provided as follows:

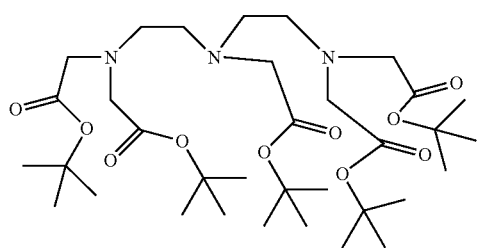

In some embodiments, the polymers described herein comprise an alkali metal. In an embodiment, the alkali metal may be sodium or potassium. In an embodiment, the alkali metal can be sodium.

The percentage of recurring units of formula (I) in the polymer conjugate, based on the total number of recurring units, may vary over a wide range. In some embodiments, the polymer may include about 100 mole % of the recurring units of formula (I). In an embodiment, the polymer may include about 1 mole % to about 99 mole % of the recurring unit of formula (I), based on the total moles of recurring units in the polymer. In an embodiment, the polymer may include about 1 mole % to about 50 mole % of the recurring unit of formula (I), based on the total moles of recurring units in the polymer. In an embodiment, the polymer may include about 1 mole % to about 30 mole % of the recurring unit of formula (I) based on the total moles of recurring units in the polymer. In an embodiment, the polymer may include about 1 mole % to about 20 mole % of the recurring unit of formula (I) based on the total moles of recurring units in the polymer. In an embodiment, the polymer may include about 1 mole % to about 10 mole % of the recurring unit of formula (I) based on the total moles of recurring units in the polymer.

In addition to comprising a recurring unit of the formula (I), the polymer may also comprise a recurring unit of the formula (II). In an embodiment, the polymer may include about 1 mole % to about 99 mole % of the recurring unit of formula (I), based on the total moles of recurring units of formulae (I) and (II). In an embodiment, the polymer may include about 1 mole % to about 50 mole % of the recurring unit of formula (I) based on the total moles of recurring units of formulae (I) and (II). In an embodiment, the polymer may include about 1 mole % to about 30 mole % of the recurring unit of formula (I) based on the total moles of recurring units of formulae (I) and (II). In an embodiment, the polymer may include about 1 mole % to about 20 mole % of the recurring unit of formula (I) based on the total moles of recurring units of formulae (I) and (II). In an embodiment, the polymer may include about 1 mole % to about 10 mole % of the recurring unit of formula (I) based on the total moles of recurring units of formulae (I) and (II).

In addition to recurring units of the formulae (I) and (II), the polymer conjugate may also include a variety of other recurring units. For example, in an embodiment, the polymer conjugate may include recurring units of the formula (III). The percentage of recurring units of formula (I), based on the total number of recurring units in a polymer conjugate comprising recurring units of formulae (I) and (III), may vary over a wide range. In an embodiment, the polymer conjugate may include about 1 mole % to about 99 mole % of the recurring unit of formula (I) based on the total moles of recurring units of formulae (I) and (III). In an embodiment, the polymer conjugate may include about 1 mole % to about 50 mole % of the recurring unit of formula (I) based on the total moles of recurring units of formulae (I) and (III). In an embodiment, the polymer conjugate may include about 1 mole % to about 30 mole % of the recurring unit of formula (I) based on the total moles of recurring units of formulae (I) and (III). In an embodiment, the polymer conjugate may include about 1 mole % to about 20 mole % of the recurring unit of formula (I) based on the total moles of recurring units of formulae (I) and (III). In an embodiment, the polymer conjugate may include about 1 mole % to about 10 mole % of the recurring unit of formula (I) based on the total moles of recurring units of formulae (I) and (III).

In an embodiment, the percentage of recurring units of formula (I), based on the total number of recurring units in a polymer conjugate comprising recurring units of formulae (I), (II), and (III) may vary over a wide range. In an embodiment, the polymer conjugate may include about 1 mole % to about 99 mole % of the recurring unit of formula (I) based on the total moles of recurring units of formulae (I), (II), and (III). In an embodiment, the polymer conjugate may include about 1 mole % to about 50 mole % of the recurring unit of formula (I) based on the total moles of recurring units of formulae (I), (II), and (III). In an embodiment, the polymer conjugate may include about 1 mole % to about 30 mole % of the recurring unit of formula (I) based on the total moles of recurring units of formulae (I), (II), and (III). In an embodiment, the polymer conjugate may include about 1 mole % to about 20 mole % of the recurring unit of formula (I) based on the total moles of recurring units of formulae (I), (II), and (III). In an embodiment, the polymer conjugate may include about 1 mole % to about 10 mole % of the recurring unit of formula (I) based on the total moles of recurring units of formulae (I), (II), and (III).

The percentage of recurring units of formula (II) in the polymer conjugate, based on the total number of recurring units in a polymer conjugate comprising recurring units of formulae (I) and (II), may also vary over a wide range. In an embodiment, the polymer may include about 1 mole % to about 99 mole % of the recurring unit of formula (II), based on the total moles of recurring units of formulae (I) and (II). In an embodiment, the polymer may include about 1 mole % to about 50 mole % of the recurring unit of formula (II) based on the total moles of recurring units of formulae (I) and (II). In an embodiment, the polymer may include about 1 mole % to about 30 mole % of the recurring unit of formula (II) based on the total moles of recurring units of formulae (I) and (II). In an embodiment, the polymer may include about 1 mole % to about 20 mole % of the recurring unit of formula (II) based on the total moles of recurring units of formulae (I) and (II). In an embodiment, the polymer may include about 1 mole % to about 10 mole % of the recurring unit of formula (II) based on the total moles of recurring units of formulae (I) and (II).

The percentage of recurring units of formula (III), based on the total number of recurring units in a polymer conjugate comprising recurring units of formulae (I) and (III), may vary over a wide range. In an embodiment, the polymer conjugate may include about 1 mole % to about 99 mole % of the recurring unit of formula (III) based on the total moles of recurring units of formulae (I) and (III). In an embodiment, the polymer conjugate may include about 1 mole % to about 50 mole % of the recurring unit of formula (III) based on the total moles of recurring units of formulae (I) and (III). In an embodiment, the polymer conjugate may include about 1 mole % to about 30 mole % of the recurring unit of formula (III) based on the total moles of recurring units of formulae (I) and (III). In an embodiment, the polymer conjugate may include about 1 mole % to about 20 mole % of the recurring unit of formula (III) based on the total moles of recurring units of formulae (I) and (III). In an embodiment, the polymer conjugate may include about 1 mole % to about 10 mole % of the recurring unit of formula (III) based on the total moles of recurring units of formulae (I) and (III).

Similarly, in an embodiment, the percentage of recurring units of formula (II), based on the total number of recurring units in a polymer conjugate comprising recurring units of formulae (I), (II), and (III), may vary over a wide range. In an embodiment, the polymer conjugate may include about 1 mole % to about 99 mole % of the recurring unit of formula (II) based on the total moles of recurring units of formulae (I), (II) and (III). In an embodiment, the polymer conjugate may include about 1 mole % to about 50 mole % of the recurring unit of formula (II) based on the total moles of recurring units of formulae (I), (II) and (III). In an embodiment, the polymer conjugate may include about 1 mole % to about 30 mole % of the recurring unit of formula (II) based on the total moles of recurring units of formulae (I), (II) and (III). In an embodiment, the polymer conjugate may include about 1 mole % to about 20 mole % of the recurring unit of formula (II) based on the total moles of recurring units of formulae (I), (II) and (III). In an embodiment, the polymer conjugate may include about 1 mole % to about 10 mole % of the recurring unit of formula (II) based on the total moles of recurring units of formulae (I), (II) and (III).

In an embodiment, the percentage of recurring units of formula (III), based on the total number of recurring units in a polymer conjugate comprising recurring units of formulae (I), (II), and (III), may vary over a wide range. In an embodiment, the polymer conjugate may include about 1 mole % to about 99 mole % of the recurring unit of formula (III) based on the total moles of recurring units of formulae (I), (II), and (III). In an embodiment, the polymer conjugate may include about 1 mole % to about 50 mole % of the recurring unit of formula (III) based on the total moles of recurring units of formulae (I), (II), and (III). In an embodiment, the polymer conjugate may include about 1 mole % to about 30 mole % of the recurring unit of formula (III) based on the total moles of recurring units of formulae (I), (II), and (III). In an embodiment, the polymer conjugate may include about 1 mole % to about 20 mole % of the recurring unit of formula (III) based on the total moles of recurring units of formulae (I), (II), and (III). In an embodiment, the polymer conjugate may include about 1 mole % to about 10 mole % of the recurring unit of formula (III) based on the total moles of recurring units of formulae (I), (II), and (III).

In an embodiment, at least one of n and m can be 1. In some embodiments, at least one n can be 1. In some embodiments, at least one n can be 2. In another embodiment, at least one of n and m can be 2. In some embodiments, at least one m can be 1. In some embodiments, at least one m can be 2.

It has been found that the amount of the agent(s), the amount of first and second drugs, and the percentage amounts of the recurring units of the formulae (I), (II), and/or (III) may be selected to advantageously control the solubility of the resulting polymer conjugate. For example, in some embodiments, the amount of the agent(s) and/or drug(s) and the percentage amounts of the various recurring units, e.g., of the formula (I), formula (II), and/or formula (III) can be selected so that the polymer conjugate is soluble (or insoluble) at a particular pH and/or pH range of interest. In some embodiments, the molecular weight of the polymer can also be selected to control solubility. For example, control over solubility may be exercised by appropriate selection of the amount of the agent, the percentage amounts of the recurring units of the formula (I), formula (II), and/or formula (III), and molecular weight. Those skilled in the art, informed by the guidance provided herein, can use routine experimentation to identify suitable amounts of the agent(s) and percentage amounts of the various recurring units that result in a polymer conjugate with desired solubility characteristics. Such control over solubility may be advantageous, depending on the application. For example, embodiments of the polymer conjugates provided herein may be used to provide improved delivery of otherwise poorly soluble anticancer drugs to selected tissues, preferably reducing undesired side effects, and/or may reduce the frequency at which a subject must undergo anticancer drug administration.

The amount of the agent(s) and/or drug(s) and the percentage amounts of the recurring units of the formulae (I), (II), and/or (III) may also be selected to provide a polymer conjugate solubility that is greater than that of a comparable polyglutamic acid conjugate that comprises substantially the same amount of the same agent(s) and/or drug(s). In an embodiment, the polymer conjugate solubility can be greater than that of a comparable polyglutamic acid conjugate. Solubility is measured by forming a polymer conjugate solution comprising at least 5 mg/mL of the polymer conjugate in 0.9 wt. % aqueous NaCl at about 22° C., and determining the optical clarity. Optical clarity may be determined turbidimetrically, e.g., by visual observation or by appropriate instrumental methods known to those skilled in the art. Comparison of the resulting solubility to a similarly formed polyglutamic acid conjugate solution shows improved solubility as evidenced by greater optical clarity over a broader range of pH values. Thus, a polymer conjugate solubility is greater than that of a comparable polyglutamic acid conjugate that comprises substantially the same amount of the agent and/or drug when a tested polymer conjugate solution, comprising at least 5 mg/mL of the polymer conjugate in 0.9 wt. % aqueous NaCl at about 22° C., has greater optical clarity over a broader pH range than that of a comparable tested polyglutamic acid conjugate solution. Those skilled in the art will understand that a "comparable" polyglutamic acid conjugate is a control material in which the polymeric portion of the conjugate has a molecular weight that is approximately the same as that of the subject polymer conjugate (comprising a recurring unit of the formula (I), a recurring unit of the formula (II), and/or a recurring unit of the formula (III)) to which it is being compared.

In an embodiment, amount of the agent(s), the amount of first and second drugs, and the percentage amounts of the recurring units of the formula (I), formula (II), and/or formula (III) can be selected to provide a polymer conjugate solubility that is greater than that of a comparable polyglutamic acid conjugate that comprises substantially the same amount of the agent(s) and/or drug(s). The range of pH values over which the polymer conjugate, comprising recurring units of the formula (I), has greater solubility than that of a comparable polyglutamic acid conjugate may be narrow or broad. As noted above, solubility is measured by forming a polymer conjugate solution comprising at least 5 mg/mL of the polymer conjugate in 0.9 wt. % aqueous NaCl at about 22° C., and determining the optical clarity. In an embodiment, the polymer conjugate is soluble over a pH range of at least about three pH units. In an embodiment, the polymer conjugate is soluble over a pH range of at least about 8 pH units. In an embodiment, the polymer conjugate is soluble over a pH range of at least about 9 pH units. In an embodiment, the pH range over which the polymer conjugate is soluble includes at least one pH value in the range of about 2 to about 5, e.g., at pH=2, pH=3, pH=4 and/or pH=5. Preferably, the pH range over which the polymer conjugate is soluble is broader than the pH range over which the comparable polyglutamic acid conjugate is soluble. For example, in an embodiment, the polymer conjugate is soluble over a pH range that is at least about one pH unit broader, preferably at least about two pH units broader, than the pH range over which the comparable polyglutamic acid conjugate is soluble.

The amount of polymer conjugate placed in solution to measure solubility can also vary greatly. In one embodiment, solubility can be measured when the tested polymer conjugate solution comprises at least about 5 mg/mL of the polymer conjugate. In an embodiment, solubility can be measured when the tested polymer conjugate solution comprises at least about 10 mg/mL of the polymer conjugate. In an embodiment, solubility is measured when the tested polymer conjugate solution comprises at least about 25 mg/mL of the polymer conjugate. In an embodiment, solubility is measured when the tested polymer conjugate solution comprises at least about 100 mg/mL of the polymer conjugate. In an embodiment, solubility can be measured when the tested polymer conjugate solution comprises at least about 150 mg/mL of the polymer conjugate. Those skilled in the art will understand that the comparable polyglutamic acid conjugate is tested at about the same concentration as that of the tested polymer conjugate.

In an embodiment, a polymer comprising a recurring unit of the formula (I) can be produced starting with polyglutamic acid and an amino acid such as asparatic and/or glutamic acid. Alternatively, in another embodiment, the polymer may be created by first converting the starting polyglutamic acid material into its salt form. The salt form of polyglutamic can be obtained by reacting polyglutamic acid with a suitable base, e.g., sodium bicarbonate. An amino acid moiety can be attached to the pendant carboxylic acid group of the polyglumatic acid. The weight average molecular weight of the polyglutamic acid is not limited, but is preferably from about 10,000 to about 500,000 daltons, and more preferably from about 25,000 to about 300,000 daltons. Such a reaction may be used to create poly-(γ-L-aspartyl-glutamine) or poly-(γ-L-glutamyl-glutamine).

In an embodiment, the amino acid can be protected by a protecting group before attachment to the polyglutamic acid. One example of a protected amino acid moiety suitable for this reaction is L-aspartic acid di-t-butyl ester hydrochloride, shown below:

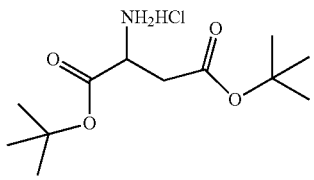

L-aspartic acid di-t-butyl ester hydrochloride

Reaction of the polyglutamic acid with the amino acid may take place in the presence of any suitable solvent. In an embodiment, the solvent can be an aprotic solvent. In a preferred embodiment, the solvent can be N,N'-dimethylformamide. In another embodiment, the solvent may be selected from the group consisting of N,N-dimethylformamide (DMF), dimethyl sulfoxide (DMSO), N-methyl-2-pyridone (NMP), and N,N-dimethylacetamide (DMAc).

A coupling agent may be used to assist the reaction to form the polymer comprising a recurring unit of the formula (I). Any suitable coupling agent may be used. In an embodiment, the coupling agent can be selected from 1-ethyl-3-(3-dimethylaminopropyl)-carbodiimide (EDC), 1,3-dicyclohexyl carbodiimide (DCC), 1,1'-carbonyl-diimidazole (CDI), N,N'-disuccinimidyl carbonate (DSC), N-[(dimethylamino)-1H-1,2,3-triazolo-[4,5-b]pyridine-1-yl-methylene]-N-methyl-methanaminium hexafluorophosphate N-oxide (HATU), 2-[(1H-benzotriazol-1-yl)-1,1,3,3-tetramethylaminium hexafluorophosphate (HBTU), 2-[(6-chloro-1H-benzotriazol-1-yl)-1,1,3,3-tetramethylaminium hexafluorophosphate (HCTU), benzotriazole-1-yl-oxy-tris-pyrrolidino-phosphonium hexafluorophosphate (PyBOP®), bromo-tris-pyrrolidino-phosphonium hexafluorophosphate (PyBroP®), 2-[(1H-benzotriazol-1-yl)-1,1,3,3-tetramethylaminium tetrafluoroborate (TBTU), and benzotriazol-1-yl-oxy-tris-(dimethylamino)phosphonium hexafluorophosphate (BOP). In an embodiment, the coupling agent is 1-ethyl-3-(3-dimethylaminopropyl)-carbodiimide (EDC).

In another embodiment, the reaction may further comprise reacting the dissolved or partially dissolved polymeric conjugate in the presence of a catalyst. Any catalyst that promotes the reaction may be used. In an embodiment, the catalyst may comprise 4-dimethylaminopyridine (DMAP).

After completion of the reaction, if the oxygen atoms of the amino acid are protected, the protecting groups can be removed using known methods such as using a suitable acid (e.g., trifluoroacetic acid). If desired, the salt form of the polymer obtained from reacting polyglutamic acid with the amino acid can be formed by treating the acid form of the polymer with a suitable base solution, e.g., sodium bicarbonate solution.

The polymer may be recovered and/or purified by methods known to those skilled in the art. For example, the solvent may be removed by suitable methods. One non-limiting example of solvent removal includes rotary evaporation. Additionally, the reaction mixture may be filtered into an acidic water solution to induce precipitation. The resultant precipitate can then be filtered, and washed with water.

In some embodiments, a polymer comprising a recurring unit of formula (I) can also include a recurring unit of formula (II) as set forth above. In other embodiments, a polymer comprising a recurring unit of formula (I) can also include a recurring unit of formula (III). In still other embodiments, a polymer comprising a recurring of formula (I) can also include a recurring unit of formula (II) and a recurring unit of formula (III).

Conjugation of a group comprising an agent, a polydentate ligand, and/or a polydentate ligand precursor with protected oxygen atoms to the polymer acid or its salt form may be carried out in various ways, e.g., by covalently bonding the group comprising an agent, a polydentate ligand, and/or a polydentate ligand precursor with protected oxygen atoms to various polymers. One method for conjugating the aforementioned groups to the polymer obtained from polyglutamic acid and/or salt is by using heat (e.g, heat from using a microwave method). Alternatively, conjugation may take place at room temperature. Appropriate solvents, coupling agents, catalysts, and/or buffers as generally known to those skilled in the art and/or as described herein may be used to form the polymer conjugate. As with polyglutamic acid, both the salt or acid form of the polymer obtained from polyglutamic acid and/or salt and an amino acid can be used as starting material for forming the polymer conjugate.

Suitable agents that can be attached or conjugated to the polymer obtained from polyglutamic acid and/or salt and an amino acid include but are not limited to drugs, optical agents, targeting agents, magnetic resonance imaging agents (e.g, paramagnetic metal compounds), stabilizing agents, polydentate ligands, and polydentate ligand precursors with protected oxygen atoms.

In one embodiment, the polymer obtained from polyglutamic acid and/or salt and an amino acid can be attached or conjugated to an optical imaging agent such as those described herein. In an embodiment, the optical agent can be Texas Red-NH$_2$.

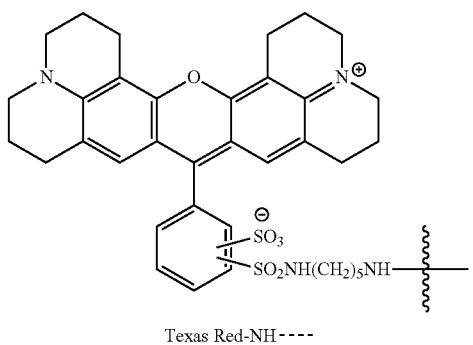

Texas Red-NH----

In one particular embodiment, reactant(s) that can form a polymer that can include at least one recurring unit of formula (I) may be reacted with DCC, Texas Red-NH$_2$ dye, pyridine, and 4-dimethylaminopyridine. The mixture is heated using a microwave method. In an embodiment, the reaction can be heated up to a temperature in the range of about 100°-150° C. In another embodiment, the time the materials are heated ranges from 5 to 40 minutes. If desired, the reaction mixture can be cooled to room temperature. Suitable methods known to those skilled in the art can be used to isolate and/or purify the polymer conjugate. For instance, reaction mixture can be filtered into an acidic water solution. Any precipitate that forms can then be filtered and washed with water. Optionally, the precipitate can be purified by any suitable method. For example, the precipitate can be transferred into acetone and dissolved, and the resulting solution can be filtered again into a sodium bicarbonate solution. If desired, the resulting reaction solution can be dialyzed in water using a cellulose membrane and the polymer can be lyophilized and isolated.

In one embodiment, the polymer obtained from polyglutamic acid and/or salt and an amino acid can be attached or conjugated to a drug (e.g., an anticancer drug). In an embodiment, the anticancer drug can be a taxane, a camptotheca, such as camptothecin, and/or an anthracycline, such as doxorubicin. In an embodiment, the anticancer drug can be a taxane such as paclitaxel or docetaxel. In some embodiments, the anticancer drug attached or conjugated to the polymer can be doxorubicin. In other embodiments, the anticancer drug attached or conjugated to the polymer can be paclitaxel. In an embodiment, paclitaxel may be joined to the polymer at the C2'-oxygen atom. In another embodiment, the paclitaxel may be joined to the polymer at the C7-oxygen atom. In another embodiment, the polymer chain comprises paclitaxel that can be coupled to the polymer only by the C2'-oxygen atom. In still another embodiment, the polymer chain comprises paclitaxel that can be coupled to the polymer only by the C7-oxygen atom. In yet another embodiment, the polymer comprises both C2'-conjugated paclitaxel groups and C7-conjugated paclitaxel groups.

The anti-cancer drug can be attached or conjugated to the polymer obtained from polyglutamic acid and/or salt and an amino acid using the methods described above with respect to Texas-Red.

In an embodiment, paclitaxel, optionally in the presence of a coupling agent (e.g, EDC and/or DCC) and a catalyst (e.g., DMAP), can be reacted with the polymer obtained from polyglutamic acid and/or salt and an amino acid in a solvent (e.g, an aprotic solvent such as DMF). Additional agents, such as pyridine or hydroxybenzotriazole may be used. In one embodiment, the reaction may take place over the period of 0.5-2 days. Suitable methods known to those skilled in the art can be used to isolate and/or purify the polymer conjugate. For example, the reaction mixture can be poured into an acidic solution to form a precipitate. Any precipitate that forms can then be filtered and washed with water. Optionally, the precipitate can be purified by any suitable method. For example, the precipitate can be transferred into acetone and dissolved, and the resulting solution can be filtered again into a sodium bicarbonate solution. If desired, the resulting reaction solution can be dialyzed in water using a cellulose membrane and the polymer can be lyophilized and isolated. The content of paclitaxel in the resulting polymer may be determined by UV spectrometry.

Alternatively, the compound comprising the agent can be reacted with an amino acid such as glutamic and/or aspartic acid in which the compound comprising the agent is coupled (e.g., covalently bonded) to the amino acid. The amino acid-agent compound can then be reacted with polyglutamic acid or its salt to form the polymer conjugate. In one embodiment, paclitaxel can be reacted with glutamic acid to form a compound in which the paclitaxel is covalently bonded to the pendant carboxylic acid group of the glutamic acid. The glutamic acid-paclitaxel compound can then be reacted with polyglutamic acid or its salt to form the polymer conjugate. In one embodiment, paclitaxel is reacted with aspartic acid to form a compound in which the paclitaxel is covalently bonded to the pendant carboxylic acid group of the aspartic acid. The aspartic acid-paclitaxel compound can then be reacted with polyglutamic acid or its salt to form the polymer conjugate. If desired, the paclitaxel coupled to the amino acid by the C2'-oxygen can be separated from the paclitaxel coupled to the amino acid by the C7-oxygen using known separation methods (e.g, HPLC).

After formation of the polymer conjugate, any free amount of agent not covalently bonded to the polymer may also be measured. For example, thin layer chromatography (TLC) may be used to confirm the substantial absence of free paclitaxel remaining in the compositions of polymers attached or conjugated to paclitaxel.

In an embodiment, the polymer obtained from polyglutamic acid and/or salt and an amino acid can be attached or conjugated to a polydentate ligand. Suitable polydentate ligands include but are not limited to diethylenetriaminepentacetic acid (DTPA), tetraazacyclododecane-1,4,7,10-tetraacetic acid (DOTA), (1,2-ethanediyldinitrilo)tetraacetate (EDTA), ethylenediamine, 2,2'-bipyridine (bipy), 1,10-phenanthroline (phen), 1,2-bis(diphenylphosphino)ethane (DPPE), 2,4-pentanedione (acac), and ethanedioate (ox). Appropriate solvents, coupling agents, catalysts, and/or buffers as generally known to those skilled in the art and/or described herein may be used to form the polymer conjugate. In another embodiment, the polymer obtained from polyglutamic acid and/or salt and an amino acid can be attached or conjugated to a polydentate ligand precursor with protected oxygen atoms. As with polyglutamic acid, both the salt or acid form of the polymer obtained from polyglutamic acid and/or salt and an amino acid can be used as starting material for forming the polymer conjugate.

In an embodiment, the polydentate ligand can be DTPA. In another embodiment, the polydentate ligand can be DOTA. In one embodiment, the polydentate ligand such as DTPA (with or without protected oxygen atoms), preferably in the presence of a coupling agent (e.g., DCC) and a catalyst (e.g., DMAP), can be reacted with the polymer obtained from polyglutamic acid and/or salt and an amino acid in a solvent (e.g, an aprotic solvent such as DMF). If protecting groups are present, removal can achieved using suitable methods. For example, the polymer conjugate with the polydentate ligand precursor with protected oxygen atoms such as DTPA with oxygen atoms protected by t-butyl groups can be treated with acid such as trifluoroacetic acid. After removal of the protecting groups, the acid can be removed by rotary evaporation. In one embodiment, DTPA can be treated with a suitable base to remove the hydrogen atoms on the carboxylic acid —OH groups. In some embodiments, the base can be sodium bicarbonate.

In an embodiment, the polymer obtained from polyglutamic acid and/or salt and an amino acid can be attached or conjugated to a targeting agent. Exemplary targeting agents include, but are not limited to, arginine-glycine-aspartate (RGD) peptides, fibronectin, folate, galactose, apolipoprotein, insulin, transferrin, fibroblast growth factors (FGF), epidermal growth factors (EGF), and antibodies. Targeting agents can be chosen such that they interact with particular receptors. For example, a targeting agent can be chosen so that it interacts with one or more of the following receptors: $\alpha_v\beta_3$-integrin, folate, asialoglycoprotein, a low-density lipoprotein (LDL), an insulin receptor, a transferrin receptor, a fibroblast growth factor (FGF) receptor, an epidermal growth factor (EGF) receptor, and an antibody receptor. In one embodiment, the arginine-glycine-aspartate (RGD) peptide can be cyclic(fKRGD).

Both the salt or acid form of the polymer obtained from polyglutamic acid and/or salt and an amino acid can be used as starting material for forming the polymer conjugate with a targeting agent. In an embodiment, the targeting agent preferably in the presence of a coupling agent (e.g, DCC) and a catalyst (e.g, DMAP), can be reacted with the polymer obtained from polyglutamic acid and/or salt and an amino acid in a solvent (e.g, an aprotic solvent such as DMF). After formation of the polymer conjugate, any free amount of agent not covalently bonded to the polymer may also be measured. For example, thin layer chromatography (TLC) may be used to confirm the substantial absence of any free targeting agent. Suitable methods known to those skilled in the art can be used to isolate and/or purify the polymer conjugate (e.g., lypholization).

In an embodiment, the polymer obtained from polyglutamic acid and/or salt and an amino acid can be attached or conjugated to a magnetic resonance imaging agent. In an embodiment, the magnetic resonance imaging agent can include a Gd(III) compound. One method for forming the magnetic resonance imaging agent is by reacting a paramagnetic metal with the polymer conjugate comprising a polydentate ligand. Suitable paramagnetic metals include but are not limited to Gd(III), Indium-111, and Yttrium-88. For example, a polymer conjugate comprising DTPA can be treated with Gd(III) in a buffer solution for a period of several hours. Suitable methods known to those skilled in the art can be used to isolate and/or purify the polymer conjugate. For instance, the resulting reaction solution can be dialyzed in water using a cellulose membrane and the polymer can be lyophilized and isolated. The amount of paramagnetic metal may be quantified by inductively coupled plasma-optical emission spectroscopy (ICP-OES) measurement.

In an embodiment, the polymer obtained from polyglutamic acid and/or salt and an amino acid can be attached or conjugated to a stabilizing agent. In some embodiments, the stabilizing agent can be polyethylene glycol. In one method, the stabilizing agent, preferably in the presence of a coupling agent (e.g, DCC) and a catalyst (e.g, DMAP), can be reacted with the polymer obtained from polyglutamic acid and/or salt and an amino acid in a solvent (e.g, an aprotic solvent such as DMF). Progress of the reaction can be measured by any suitable method such as TLC. The resulting polymer conjugate can be purified using methods known to those skilled in the art such as dialysis.

The polymer conjugates may be used to deliver an imaging agent, targeting agent, magnetic resonance imaging agent and/or a drug to a selected tissue. For example, polymer conjugates comprising the Texas Red dye may be used to deliver an imaging agent to a selected tissue. In one embodiment, the polymer conjugates comprising at least one recurring unit of the formula (I) can be used to treat or ameliorate a disease or condition such as cancer. In an embodiment, the polymer conjugates described herein can be used to diagnose a disease or condition (e.g., cancer). In yet one more embodiment, the polymer conjugates described herein can be used to image a portion of tissue. In some embodiments, the disease or condition can be a cancer such as lung cancer, breast cancer, colon cancer, ovarian cancer, prostate cancer, and melanoma. In an embodiment, the disease or condition can be a tumor selected from lung tumor, breast tumor, colon tumor, ovarian tumor, prostate tumor, and melanoma tumor. In some embodiments, the tissue being imaged can be tissue from lung tumor, breast tumor, colon tumor, ovarian tumor, prostate tumor, and/or melanoma tumor.

Multiple compounds that comprise an agent can be attached or conjugated to a polymer conjugate comprising a recurring unit of formula (I). In some embodiments, the agents can be different. For example, a compound that comprises a targeting agent can be attached or conjugated to a polymer comprising a recurring unit formula (I). The resulting polymer can then be reacted with a compound that comprises an imaging agent to form a polymer conjugate comprising a recurring unit formula (I) that includes both a targeting and imaging agent. If desired, the polymer conjugate with a targeting and imaging agent can be further reacted with a compound comprising a stabilizing agent to thereby conjugate the stabilizing agent to the polymer.

In an embodiment, the polymers described above may be formed into nanoparticles in aqueous solution. In an embodiment, conjugates comprising a polymer and a drug may be formed into nanoparticles in a similar manner. In an embodiment, such nanoparticles may be used to deliver a drug to a selected tissue.

Compositions comprising hydrophobic compounds and a polymer comprising a recurring unit of the formula (I) may be prepared in various ways. In an embodiment, a method of making the composition can include the steps of reacting the dissolved or partially dissolved polymer conjugate having the second hydrophobic compound already attached with a first hydrophobic compound, for example, the first hydrophobic drug, to form a mixture.

An embodiment provides a method of making the composition, that can include the steps of partially dissolving the polymer conjugate in a solvent, and intermixing a first hydrophobic drug with the at least partially dissolved polymer conjugate to form a mixture. In an embodiment, the method further can include the step of drying the mixture to form the composition in a dry form. In an embodiment, the intermixing step comprises mixing a solution of the first hydrophobic drug with the at least partially dissolved polymer conjugate to form the mixture.

The polymer conjugate may be dissolved or partially dissolved in a variety of solvents to prepare it for mixture with the first hydrophobic drug. In an embodiment, the solvent can include a hydrophilic solvent, such as a polar solvent. Suitable polar solvents include protic solvents such as water, methanol, ethanol, propanol, isopropanol, butanol, formic acid, and acetic acid. Other suitable polar solvents include aprotic solvents, such as acetone, acetonitrile, dimethylformamide, dimethyl sulfoxide, tetrahydrofuran, and 1,4-dioxane. In an embodiment, the solvent can be an aqueous solvent, for example, water.

Dissolving or partial dissolving the polymer conjugate in a solvent may be further aided by the use of conventional mechanical techniques. For instance, the polymer conjugate may be shaken or stirred in the solvent to induce dissolving or partial dissolving. In an embodiment, the polymer and solvent are sonicated. Sonication is the act of applying sound energy, for example, ultrasound energy, to agitate the particles in a sample. Sonication may take place using, for example, an ultrasonic bath or an ultrasonic probe. The degree to which the polymer is dissolved may be controlled by varying the intensity and duration of the mechanical shaking or stirring or the sonication conditions. Shaking, stirring, or sonicating may take place over any duration of time. For example, the mixture may be sonicated for a period of time ranging between several seconds to several hours. In an embodiment, the polymer conjugate is sonicated in the solvent for a period of time ranging between about 1 minute and about 10 minutes. In an embodiment, the polymer conjugate is sonicated in the solvent for about 5 minutes.

In an embodiment, the first hydrophobic drug can be added to the polymer conjugate solution. The first hydrophobic drug may or may not be dissolved or partially dissolved in a variety of solvents before it is mixed with the polymer conjugate. If the hydrophobic drug is dissolved or partially dissolved in a solvent, the solvent may include a hydrophilic solvent, such as a polar solvent. Suitable polar solvents include protic solvents such as water, methanol, ethanol, propanol, isopropanol, butanol, formic acid, acetic acid, and acetone. Other suitable polar solvents include aprotic solvents, such as acetone, acetonitrile, dimethylformamide, dimethyl sulfoxide, tetrahydrofuran, and 1,4-dioxane. In an embodiment, the first hydrophobic drug can be dissolved or partially dissolved in an alcohol. In an embodiment, the first hydrophobic drug can be dissolved or partially dissolved in ethanol.

After the first hydrophobic drug is added to the polymer conjugate solution, for example, by using a pipette, additional mixing may be performed. For instance, the polymer conjugate and first hydrophobic drug solution may be shaken or stirred. In an embodiment, the polymer conjugate and first hydrophobic drug solution can be sonicated. Shaking, stirring, or sonicating may take place over any duration of time. For instance, the mixture may be sonicated for a period of time ranging between several seconds to several hours. In an embodiment, the polymer conjugate and first hydrophobic drug solution can be sonicated for a period of time ranging between about 1 minute and about 10 minutes. In an embodiment, the polymer conjugate and first hydrophobic drug solution can be sonicated for about 5 minutes.

In an embodiment, the polymer conjugate and first hydrophobic drug can be mixed together before either is dissolved in a solvent. In an embodiment, a solvent or mixture of solvents may be added to the mixture of the polymer conjugate and first hydrophobic drug. After the solvent or mixture of solvents is added to the polymer conjugate and first hydrophobic drug, one of or both of the polymer conjugate and first hydrophobic drug may dissolve or partially dissolve. In an embodiment, the polymer conjugate encapsulates or partially encapsulates the first hydrophobic drug. The solvent or mixture of solvents may comprise one or more of water, methanol, ethanol, propanol, isopropanol, butanol, formic acid, acetic acid, acetone, acetonitrile, dimethylformamide, dimethyl sulfoxide, tetrahydrofuran, and 1,4-dioxane. In an embodiment, the mixture of solvents comprises an alcohol and water. In an embodiment, the mixture of solvents comprises ethanol and water.

The composition comprising a first hydrophobic drug, a second hydrophobic drug, and a polymer conjugate as described herein forms after sufficient mixture. Optionally, the composition may then be isolated and/or purified. Suitable methods known to those skilled in the art can be used to isolate and/or purify the polymer conjugate and encapsulated (or partially encapsulated) first hydrophobic drug. The composition may then be dried by any suitable method known to those skilled in the art. For example, in one embodiment, the composition is freeze-dried. The conditions of freeze-drying the composition may vary. In an embodiment, the mixture is freeze-dried at a temperature ranging between about −30° C. to about −10° C. In an embodiment, the mixture is freeze-dried at a temperature of about −20° C. Once the composition has been optionally isolated and dried, it may then be stored in appropriate conditions. For example, the composition may be stored in at a temperature suitable for freeze-drying, as set forth above.

In some embodiments, prodrugs, metabolites, stereoisomers, hydrates, solvates, polymorphs, and pharmaceutically acceptable salts of the compounds disclosed herein (e.g., the compositions, polymer conjugate, hydrophobic drug(s) and/or any agent that the polymer conjugate comprises) are provided.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compounds disclosed herein (e.g., the compositions, polymer conjugate, hydrophobic drug(s) and/or the agent that the polymer conjugate comprises) can be used alone, in combination with other compounds disclosed herein, or in combination with one or more agents active in the therapeutic areas described herein.

In another aspect, the present disclosure relates to a pharmaceutical composition comprising one or more physiologically acceptable surface active agents, carriers, diluents, excipients, smoothing agents, suspension agents, film forming substances, and coating assistants, or a combination thereof; and a compound (e.g., the compositions, polymer conjugate, hydrophobic drug(s) and/or the agent that the polymer conjugate comprises) disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetatemethacrylate copolymer as a derivative of polyvinyl may be used as suspension agents; and plasticizers such as ester phthalates and the like may be used as suspension agents.

The term "pharmaceutical composition" refers to a mixture of a compound disclosed herein (e.g., the compositions, polymer conjugate, hydrophobic drug(s) and/or the agent that the polymer conjugate comprises) with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" refers to chemical compounds diluted in water that dissolves the compound of interest (e.g., the compositions, polymer conjugate, hydrophobic drug(s) and/or the agent that the polymer conjugate comprises) as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. The term "physiologically acceptable" refers to a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds (e.g., the polymer conjugate and/or the agent that it comprises) can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions.

Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds (e.g., the compositions, polymer conjugate, hydrophobic drug(s) and/or the agent that the polymer conjugate comprises) in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds (e.g., the compositions, polymer conjugate, hydrophobic drug(s) and/or the agent that the polymer conjugate comprises) can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients (e.g., the compositions, polymer conjugate, hydrophobic drug(s) and/or the agent that the polymer conjugate comprises) in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions (e.g., the compositions, polymer conjugate, hydrophobic drug(s) and/or the agent that the polymer conjugate comprises) may take the form of tablets or lozenges formulated in conventional manner.

For administration by inhalation, the compounds (e.g., the compositions, polymer conjugate, hydrophobic drug(s) and/or the agent that the polymer conjugate comprises) for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds (e.g., the compositions, polymer conjugate, hydrophobic drug(s) and/or the agent that the polymer conjugate comprises) in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds (e.g., the compositions, polymer conjugate, hydrophobic drug(s) and/or the agent that the polymer conjugate comprises) may also be formulated in rectal compositions such as suppositories or retention enemas, e.g., containing conventional suppository bases such as cocoa butter or other glycerides.

In addition to the formulations described previously, the compounds (e.g., the compositions, polymer conjugate, hydrophobic drug(s) and/or the agent that the polymer conjugate comprises) may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few hours or weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes are targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

The compositions described herein (e.g., the compositions, polymer conjugate, hydrophobic drug(s) and/or the agent that the polymer conjugate comprises) may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the active compound into contact with living tissue.

Compositions suitable for administration (e.g., the compositions, polymer conjugate, hydrophobic drug(s) and/or the agent that the polymer conjugate comprises) include compositions where the active ingredients are contained in an amount effective to achieve its intended purpose. The therapeutically effective amount of the compounds disclosed herein required as a dose depends on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are typically commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the compositions described herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered compositions described herein, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by conventional prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein (e.g., the compositions, polymer conjugate, hydrophobic drug(s) and/or the agent that the polymer conjugate comprises) can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular composition may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions described herein may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions as described herein formulated in a compatible pharmaceutical carrier may also be prepared, placed in an appropriate container, and labeled for treatment of an indicated condition.

Polymers and copolymers comprising a recurring unit of the formula (I) may have many different uses. An embodiment provides a method of treating or ameliorating a disease or condition comprising administering an effective amount of one or more polymer conjugates described herein or the pharmaceutical composition described herein to a mammal in need thereof. Another embodiment provides a use an effective amount of one or more polymer conjugates described herein or the pharmaceutical composition described herein for treating or ameliorating a disease or condition. In an embodiment, the disease or condition is selected from lung tumor, breast tumor, colon tumor, ovarian tumor, prostate tumor, and melanoma tumor. In an embodiment, the disease or condition is selected from lung cancer, breast cancer, colon cancer, ovarian cancer, prostate cancer, and melanoma.

An embodiment provides a method of diagnosing a disease or condition comprising administering an effective amount of one or more polymer conjugates described herein or the pharmaceutical composition described herein to a mammal in need thereof. Another embodiment provides a use an effective amount of one or more polymer conjugates described herein or the pharmaceutical composition described herein for diagnosing a disease or condition. In an embodiment, the disease or condition is selected from lung tumor, breast tumor, colon tumor, ovarian tumor, prostate tumor, and melanoma tumor. In an embodiment, the disease or condition is selected from lung cancer, breast cancer, colon cancer, ovarian cancer, prostate cancer, and melanoma.

An embodiment provides a method of imaging a portion of tissue comprising contacting a portion of tissue with an effective amount of one or more polymer conjugates described herein or the pharmaceutical composition described herein. Another embodiment provides a use an effective amount of one or more polymer conjugates described herein or the pharmaceutical composition described herein for imaging a portion of tissue. In some embodiments, the tissue being imaged can be tissue from lung tumor, breast tumor, colon tumor, ovarian tumor, prostate tumor, and/or melanoma tumor.

EXAMPLES

The following examples are provided for the purposes of further describing the embodiments described herein, and do not limit the scope of the invention.

Materials

Poly-L-glutamate sodium salts with different molecular weights (average molecular weights of 41,400 (PGA(97 k)), 17,600 (PGA(44 k)), 16,000 (PGA(32 k)), and 10,900 (PGA (21 k)) daltons based on multi-angle light scattering (MALS)); N-(3-dimethylaminopropyl)-N'-ethylcarbodiimide hydrochloride (EDC); hydroxybenzotriazole (HOBt); pyridine; 4-dimethylaminopyridine (DMAP); N,N'-dimethylformamide (DMF); gadolinium-acetate; chloroform; camptothecin, and sodium bicarbonate were purchased from Sigma-Aldrich Chemical company. Poly-L-glutamate was converted into poly-L-glutamic acid using 2 N hydrochloric acid solution. Trifluoroacetic acid (TFA) was purchased from Bioscience. L-glutamic acid di-t-butyl ester hydrochloride (H-Glu(OtBu)-OtBu.HCl), N-α-CBZ-L-glutamic acid α-benzyl ester (Z-Glu-OBzl) were purchased from Novabiochem (La Jolla, Calif.). Paclitaxel was purchased from PolyMed (Houston, Tex.). $^3$H-paclitaxel was purchased from Moravek Biochemicals, Inc. Sulforhodamine B dye for cytotoxic MTT test (cell viability) was purchased from Molecular Imaging Products Company (Michigan). The chemical p-NH$_2$-Bn-DPTA-penta-(t.-Bu ester) was purchased from Macrocyclics (Dallas, Tex.).

$^1$H NMR was obtained from Joel (400 MHz), and particle sizes were measured by ZetalPals (Brookhaven Instruments Corporation). Microwave chemistry was carried out in Biotage. Molecular weights of polymers were determined by size exclusion chromatography (SEC) combined with a multi-angle light scattering (MALS) (Wyatt Corporation) detector. The content of paclitaxel in polymer-paclitaxel conjugates was estimated by UV/Vis spectrometry (Lambda Bio 40, PerkinElmer) based on a standard curve generated with known concentrations of paclitaxel in methanol ($\lambda$=228 nm).

A poly-(γ-L-glutamyl-glutamine) were prepared from a polyglutamate sodium salt, according to the procedures described in U.S. Patent Publication No. 2007-0128118, filed Dec. 1, 2006, which is hereby incorporated by reference in its entirety, and particularly for the purpose of describing the syntheses of the polymer described therein (e.g, poly-(γ-L-glutamyl-glutamine), poly-(γ-L-aspartyl-glutamine), poly-(γ-L-glutamyl-glutamine)-poly-L-glutamic acid, and poly-(γ-L-aspartyl-glutamine)-poly-L-glutamic acid. Poly(β-aspartyl-glutamine)-paclitaxel conjugates (PGA-21-A-paclitaxel-20) and poly(γ-glutamyl-glutamine)-paclitaxel conjugates (PGA-21-G-paclitaxel-20 and PGA-32-G-paclitaxel-20) were prepared according to the procedures described in U.S. Patent Publication No. 2007-0128118, filed Dec. 1, 2006. Synthesis of poly-L-glutamate-paclitaxel conjugates (PGA-PTX) was carried out as reported in previous literature. See Li et al. "Complete Regression of Well-established tumors using a novel water-soluble poly(L-glutamic acid)-paclitaxel conjugate." *Cancer Research* 1998, 58, 2404-2409, the contents of which are herein incorporated by reference in its entirety.

Average molecular weights of the polymers were determined using the system and conditions described below (hereinafter, referred to as the Heleos system with MALS detector).

SEC-MALS Analysis Conditions:
    HPLC system: Agilent 1200
    Column: Shodex SB 806M HQ (exclusion limit for Pullulan is 20,000,000, particle size: 13 micron, size (mm) ID×Length; 8.0×300)
    Mobile Phase: 1×DPBS or 1% LiBr in DPBS (pH7.0)
    Flow Rate: 1 ml/min
    MALS detector: DAWN HELEOS from Wyatt
    DRI detector: Optilab rEX from Wyatt
    On-line Viscometer: ViscoStar from Wyatt
    Software: ASTRA 5.1.9 from Wyatt
    Sample Concentration: 1-2 mg/ml
    Injection volume: 100 μl
    dn/dc value of polymer: 0.185 was used in the measurement.

BSA was used as a control before actual samples are run.

Example 1

First Paclitaxel Formulation Using PGA-21-G-Paclitaxel-20:

PGA-21-G-paclitaxel-20 (110 mg), which was prepared from a starting polymer of poly-(γ-glutamyl)-poly-L-glutamine-19,800 and having a content of paclitaxel of 20% weight by weight, was dissolved in distilled water (3 mL). The sample was sonicated for 5 minutes. Then, a solution of paclitaxel (22 mg) in ethanol (0.4 mL) was added into the sample using a pipette. The solution mixture was then sonicated for an additional 5 minutes. The resulting mixture was freeze-dried and stored at −20° C. before further experimentation.

Example 2

Second Paclitaxel Formulation Using PGA-21-G-Paclitaxel-20:

PGA-21-G-paclitaxel-20 (110 mg) was dissolved in distilled water (3 mL). The sample was sonicated for 5 minutes.

Then, a solution of paclitaxel (11 mg) in ethanol (0.4 mL) was added into the sample using a pipette. The solution mixture was then sonicated for an additional 5 minutes. The resulting mixture was freeze-dried and stored at −20° C. before further experiments.

Example 3

Paclitaxel Formulation Using PGA-32-G-Paclitaxel-20:

PGA-32-G-paclitaxel-20 (110 mg), which was prepared from a starting polymer of poly-(γ-glutamyl)-poly-L-glutamine-37,400 and having a content of paclitaxel of 20% weight by weight, was dissolved in distilled water (3 mL). The sample was sonicated for 5 minutes. Then, a solution of paclitaxel (22 mg) in ethanol (0.4 mL) was added into the sample using a pipette. The solution mixture was sonicated for an additional 5 minutes. The resulting mixture was freeze-dried and stored at −20° C. before further experiments.

Example 4

First Control Paclitaxel Formulation Using Ethanol:Cremophor®:

A non-polymeric control sample was created by dissolving paclitaxel in a one-to-one ratio solution of ethanol and Cremophor, which is a polyethoxylated castor oil (a mixture of ricinoleic acid, polyglycol ester, glyerol polyglycol esters, and polyglycols), at a concentration of 30 mg/mL. Before this solution was used in the testing, it was further diluted with saline to a concentration of 6 mg/mL immediately before injection.

Example 5

Third Paclitaxel Formulation Using PGA-21-G-Paclitaxel-20 for Pharmacokinetics and Pharmacodynamics:

PGA-21-G-paclitaxel-20 (110 mg) was dissolved in distilled water (3 mL). The sample was sonicated for 5 minutes. Then, a solution of paclitaxel (22 mg) in ethanol (0.5 mL) and $^3$H-paclitaxel 220 μl (1 mCi/mL) (tritium is for detection purposes) was added into the sample using a pipette. The final volume of the solution was adjusted with distilled water to become 4 mL. The solution mixture was sonicated for an additional 5 minutes. The solution was divided into 5 small individual vials (0.8 mL/vial). The samples in the vials were freeze-dried and stored at low temperature (−20° C.) before further experimentation.

Example 6

Second Control Paclitaxel Formulation Using Ethanol:Cremophor® for PKPD:

A control sample was created by dissolving paclitaxel (22 mg) in a one-to-one ratio solution of ethanol and Cremophor at a concentration of 30 mg/mL and $^3$H-paclitaxel 220 ul (1 mCi/mL) (tritium is for detection purposes) was added into the sample using a pipette. Before this solution was used in the testing, it was further diluted with saline to a concentration of 6 mg/mL immediately before injection.

Example 7

Cell Culture and Preparation:

B16F0 cells were purchased from ATCC(CRL-6322, ATCC American Type Culture Collection, Rockville, Md.) and were grown in Dulbecco's modified Eagle's medium (DMEM) with 10% fetal bovine serum and 100 units/mL of penicillin. The cells were grown in an environment at 37° C. in 5% $CO_2$. The culture medium was removed and discarded. The cells were rinsed with Dulbecco Phosphate Buffer Solution (DPBS) and then Trypsin-ethylenediaminetetra-acetic acid (EDTA) solution (0.5 ml) was added to the cells. Dispersion of the cells was assured by observing them under an inverted microscope. Complete growth medium (6.0 to 8.0 ml) was then added, and the cells were aspirated by gently pipetting. The cell suspension in appropriate aliquots was transferred to new culture plates. The cells were allowed to grow at 37° C. in 5% $CO_2$ for 24 hours before further experiments.

Example 8

In Vitro Cytotoxicity MTT Studies

Formulations prepared as in Examples 1-4 were reconstituted with saline (0.9% NaCl in sterile water) at a concentration of 6 mg/mL based on paclitaxel. These formulations described herein containing paclitaxel were evaluated for their effect on the proliferation of B16F0 melanoma cells at several different concentrations of the drug. Cytotoxic MTT assay was carried out as reported in Monks et al. *JNCI* 1991, 83, 757-766, which is hereby incorporated by reference in its entirety.

Example 9

Animals and Tumor Models for Pharmacokinetic Studies

Nude mice (6-7 weeks old, body weight 25-30 grams, female) were purchased from Charles River Lab (Willington, Mass.). B16F0 cell lines were purchased from ATCC(CRL-6322, ATCC American Type Culture Collection, Rockville, Md.). The B16F0 cells were cultured in DMEM supplemented with 10% Fetal bovine serum, 2 μM Glutamine, 1 mM non-essential amino acids, 1 mM sodium pyruvate, 100 U/ml penicillin and 100 ug/ml streptomycin. The B16F0 cells harvested from tissue culture were counted and re-suspended to a concentration of $5 \times 10^6$ per mL. Using a TB syringe, 0.4 mL of cell-containing solution (a total of $2 \times 10^6$ cells) was administered via subcutaneous injection into each mouse. Four tumors were inoculated per animal. The locations of the tumors were the right shoulder, the left shoulder, the right hip, and left hip.

Example 9a

The formulation prepared in Example 5 was reconstituted with saline (0.9% NaCl in sterile water) to a paclitaxel concentration of 6 mg/mL. Once the mean tumor volume for the entire population of mice from Example 9 had reached 200-300 $mm^3$ (6-8 mm diameter), each tumor bearing animal received a single IV bolus injection of either a formulation of paclitaxel using PGA-21-G-paclitaxel-20 as described in Example 5 at 20 mg/kg, or a formulation of paclitaxel using ethanol and Cremophor as described in Example 6 at 20 mg/kg. For each drug, groups of 4 mice were anesthetized at various points in time. The anesthetized times were (in hours): 0.5, 2, 4, and 24.

Figure 2:
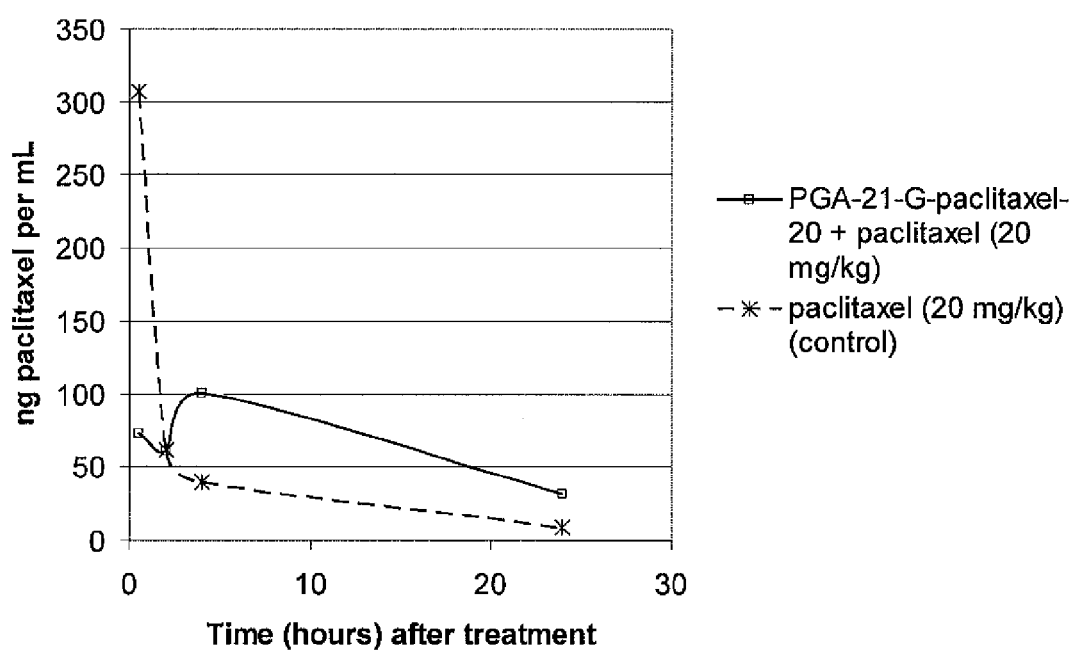
FIG. 2 shows a comparison of the paclitaxel plasma concentration between a composition comprising paclitaxel as described herein and a conventional formulation of paclitaxel.

Blood was collected into heparinized tubes in an amount of 0.5 ml via cardiac or retro-orbital puncture. Thereafter, the mice were sacrificed before recovering from anesthesia. The blood samples of each mouse were centrifuged at 11,000 rpm. The supernatant plasma (0.2-0.3 mL) from the blood samples were collected and transferred into a new vial. A 0.1 mL sample of the plasma of each sample was separately transferred into a new 10-mL vial, and a liquid scintillation solution (5 mL) was added to the vial. The content of paclitaxel was analyzed using a liquid scintillation LS6500 counting system (Beckman) and calculated from the standard curve of each sample. The results are shown in FIG. 2.

The paclitaxel concentration of the formulation of paclitaxel using PGA-21-G-paclitaxel-20 remained much higher over a longer period of time than the control sample. These results indicate that the new formulation of paclitaxel using PGA-21-G-paclitaxel-20 has longer term effectiveness in blood circulation than compared to a formulation of paclitaxel using ethanol and Cremophor.

Example 9b

Figure 3:
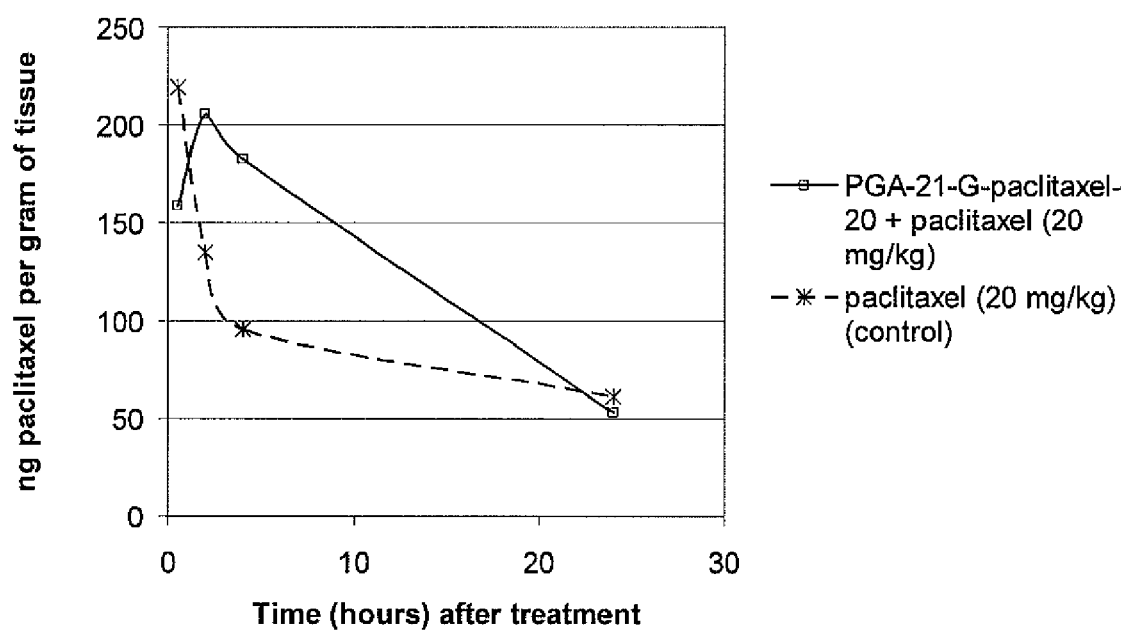
FIG. 3 shows a comparison of the paclitaxel tumor concentration between a composition comprising paclitaxel as described herein and a conventional formulation of paclitaxel.

The formulation prepared as in Example 5 was reconstituted with saline (0.9% NaCl in sterile water) to a paclitaxel concentration of 6 mg/mL. Once the mean tumor volume for the entire population of mice from Example 9 had reached 200-300 mm³ (6-8 mm diameter), each tumor bearing animal received a single IV bolus injection of a formulation of paclitaxel using PGA-21-G-paclitaxel-20 as described in Example 5 at 20 mg/kg, or a formulation of paclitaxel using ethanol and Cremophor as described in Example 6 at 20 mg/kg. For each drug, groups of 4 mice were anesthetized at various points in time. The anesthetized times were (in hours): 0.5, 2, 4, and 24. Tumors from the two hips and the two shoulders were harvested independently. Thereafter, the mice were sacrificed before recovering from anesthesia. Approximately 80-180 mg of each tumor was placed in a scintillation vial, and the tumor was digested with Soluene (tissue solubilzer) (1 mL). Then, 0.1 mL of digested tissue was transferred into a 10-mL vial, and a liquid scintillation cocktail (5 mL) was added to the vial. The content of paclitaxel was analyzed using a liquid scintillation LS6500 counting system (Beckman) and calculated from the standard curve of each sample. The results are shown in FIG. 3.

The paclitaxel tumor accumulation of a formulation using PGA-21-G-paclitaxel-20 remained much higher than the control sample over a longer period of time. These results indicate that the formulation of paclitaxel from using PGA-21-G-paclitaxel-20 has improved accumulation in tumors compared to the formulation of paclitaxel using ethanol and Cremophor.

Example 10

Animals and Tumor Models for In Vivo Efficacy Studies

Nude mice (6-8 weeks old, body weight 21-25 grams, male) were purchased from Charles River Lab (Willington, Mass.). B16-F0-EGFP stable cells were maintained in a cell culture grown in DMEM supplemented with 10% Bovine Serum, 100 U/ml of penicillin and 100 of µg/ml streptomycin. Cells were split 48 hours before inoculation so that they were in a log phase growth upon being harvested. Cells were harvested from the tissue culture using trypsin-EDTA and the number of viable cells was determined by counting in a hemocytometer in the presence of trypan blue. The cells were suspended to a concentration of $5 \times 10^6$ per ml in a DMEM media without serum. The tumor cell suspension was then inoculated using a 1 cc insulin syringe at a concentration of $5 \times 10^6$ cells per ml over each shoulder and each hip by injecting 0.1 ml of the tumor cell suspension (4 sites per mouse).

On the day of tumor inoculation, the mice were sequentially placed into one of 6 groups and housed 3 mice to a cage with a total number of 12 cages. Each mouse was ear punched while under anesthesia at the time of tumor inoculation so that it could be uniquely identified throughout the experiment. Each cage was labeled with the drug, drug dose administered to the animals it contained, and the number of animals it contained.

Example 10a

The weight loss toxicity at the maximum tolerance dose (MTD) of polymers made in accordance with Example 1 was measured. MTD is defined herein as the dose that produces a maximum 15% body weight loss within 2 weeks. A formulation prepared as in Example 1 was reconstituted with saline (0.9% NaCl in sterile water) at a concentration of 50 mg/mL based on PGA-21-G-paclitaxel-20. The positive control for this example was the anti-cancer drug, PGA-21-G-paclitaxel-20. Saline was also used as a negative control with no anti-tumor drug.

Figure 4:
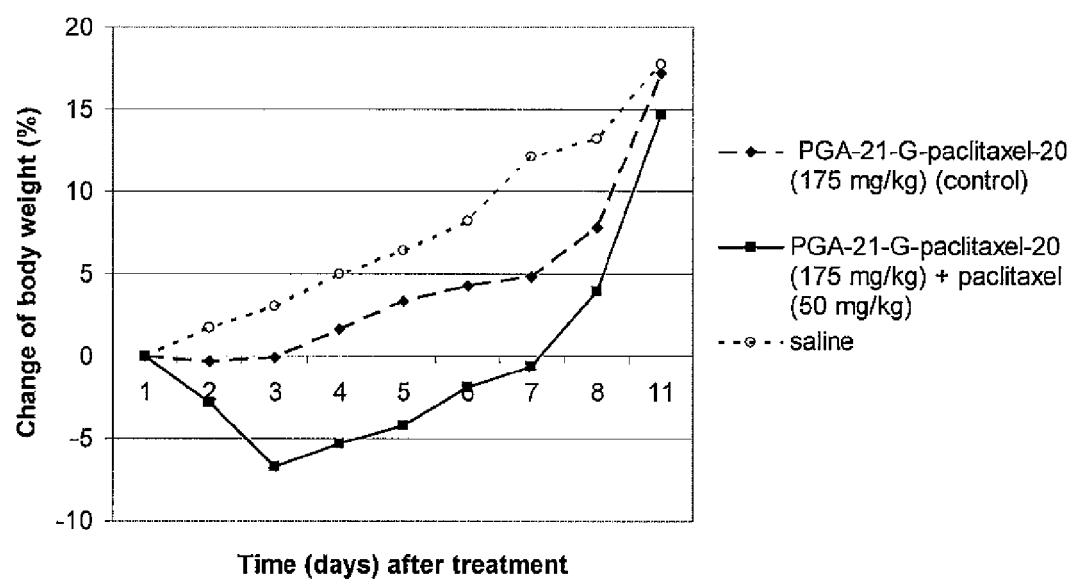
FIG. 4 shows the change of body weight in mice upon treatment with a composition comprising paclitaxel as described herein compared to a positive control and a negative control.

The actual amount of drug injected into the animal was determined in accordance with the body weight of each animal. The first dose of drug was given to the mice when the average tumor size of the entire population of mice reached about 15 to about 50 mm³ (tumor size was estimated from the formula $(w^2 \times 1)/2$ where "1" is the longest diameter of the tumor and "w" is the diameter perpendicular to the longest diameter measured in millimeters). The mice received 2 doses of drug on two consecutive days via tail vein injection and the administration was without anesthesia. Stock solutions were prepared fresh on the day of injection. Drug stock solutions were drawn into a 1-cc syringe and injected intravenously. Mice were weighed to the nearest 0.1 g. Nude nu/nu mice were injected with high dosage amounts of either the PGA-21-G-20 polymer alone at a dose of 175 mg/kg or the formulation of paclitaxel with PGA-21-G-20 polymer at a dose of 225 mg/kg. The change of body weight (%) upon treatment of each drug was independently observed and recorded over time (days). The results are shown in FIG. 4.

The formulation of paclitaxel combined with PGA-21-G-paclitaxel-20 showed a comparable body weight loss at a much higher dosage compared to the PGA-21-G-paclitaxel-20 alone. These results indicate that formulations using PGA-21-G-20 of the present invention is less toxic to mice than the control samples.

Example 10b

In Vivo Efficacy Studies

The antitumor effects of a formulation of paclitaxel combined with PGA-21-G-20 polymer and PGA-21-G-20 polymer alone at the maximum tolerance dose (MTD) on B16F0-EGF melanoma tumors in nude nu/nu mice as described in Example 10 over time were measured. Saline was used as a negative control. A formulation as prepared in Example 1 was reconstituted with saline (0.9% NaCl in sterile water) at a concentration of 50 mg/mL based on PGA-21-G-paclitaxel-20. The positive control in this example was the anti-cancer drug, PGA-21-G-paclitaxel-20. Saline was used as the negative control with no anti-tumor drug.

Figure 5:
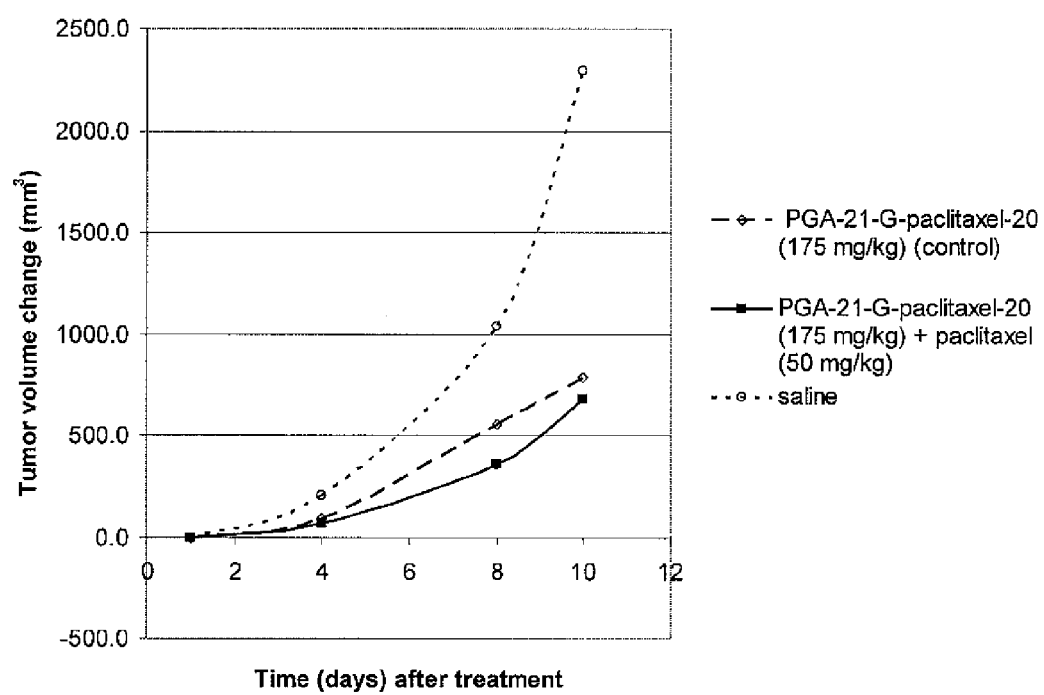
FIG. 5 shows the antitumor effect in mice upon treatment with a composition comprising paclitaxel as described herein compared to a positive control and a negative control.

The actual amount of drug injected into the animal was determined in accordance with the body weight of each animal. The first dose of drug was given to the mice when the average tumor size of the entire population of mice in the study reached 15 to 50 mm³. Mice received 2 doses of drug on two consecutive days via intravenous injection into the tail vein without anesthesia. Stock solutions were prepared fresh on the day of injection. The drug stock solutions were drawn into a 1-cc syringe and injected intravenously. The tumor size was measured to the nearest 0.1 mm. Nude nu/nu mice were injected with high dosage amounts of either PGA-21-G-20 polymer at a dose of 175 mg/kg or the formulation of paclitaxel with PGA-21-G-20 at a dose of 225 mg/kg. The change of tumor volume upon treatment of each drug was independently observed and recorded over time (days). The results are shown in FIG. 5.

The formulation of paclitaxel combined with PGA-21-G-20 significantly inhibited the tumor growth. These results indicate that compositions of a first hydrophobic drug, a second hydrophobic drug, and a polymer conjugate as described herein are effective anti-cancer agents.

It will be understood by those of skill in the art that numerous and various modifications can be made without departing from the spirit of the present invention. Therefore, it should be clearly understood that the forms of the present invention are illustrative only and not intended to limit the scope of the present invention.

What is claimed is:

1. A composition comprising a first anticancer drug, a second anticancer drug and a polymer conjugate, wherein:
   the polymer conjugate comprises a polymeric matrix that non-covalently entraps at least a portion of the first anticancer drug therein;
   the polymer conjugate comprises a recurring unit of the formula (I):

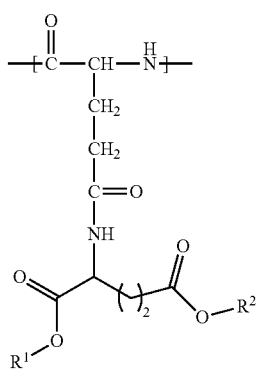

wherein:
one of $R^1$ and $R^2$ is the second anticancer drug; and
the other one of $R^1$ and $R^2$ is hydrogen or an alkali metal.

2. The composition of claim 1, wherein the polymer conjugate further comprises a recurring unit of the formula (II):

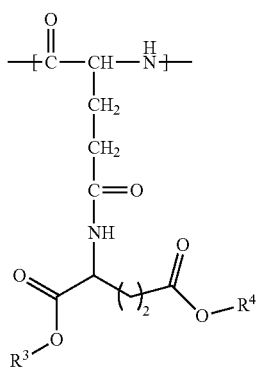

wherein each $R^3$ and each $R^4$ are each independently hydrogen or an alkali metal.

3. The composition of claim 1, wherein the polymer conjugate further comprises a recurring unit of the formula (III):

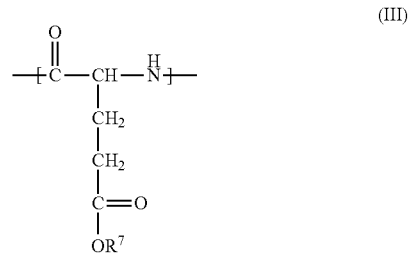

wherein each $R^7$ is hydrogen or an alkali metal.

4. The composition of claim 3, wherein the polymer conjugate includes include about 1 mole % to about 50 mole % of the recurring unit of formula (III) based on the total moles of recurring units of formulae (I) and (III).

5. The composition of claim 1, wherein the first anticancer drug has a chemical structure that is the same as that of the second anticancer drug.

6. The composition of claim 1, wherein the first anticancer drug and the second anticancer drug are independently selected from the group consisting of a taxane, a camptotheca, and an anthracycline.

7. The composition of claim 6, wherein the first anticancer drug and the second anticancer drug is a taxane.

8. The composition of claim 7, wherein the first anticancer drug and the second anticancer drug is a paclitaxel.

9. The composition of claim 2, wherein the number of recurring units of the formula (I) and the number of recurring units of formula (II) in the polymer conjugate are each independently in the range of from about 50 to about 5,000.

10. The composition of claim 2, wherein the number of recurring units of the formula (I) and the number of recurring units of formula (II) in the polymer conjugate are each independently in the range of from about 100 to about 2,000.

11. The composition of claim 2, wherein the polymer conjugate consists of a recurring unit of formula (I) and a recurring unit of formula (II).

12. The composition of claim 1, wherein the first anticancer drug is present in an amount in the range of about 5% to about 40% (weight/weight) based on the mass ratio of the first anticancer drug to the combined weight of the first anticancer drug and the polymer conjugate.

13. The composition of claim 1, wherein the first anticancer drug is present in an amount in the range of about 10% to about 30% (weight/weight) based on the mass ratio of the first anticancer drug to the combined weight of the first anticancer drug and the polymer conjugate.

14. The composition of claim 1, wherein the polymer conjugate comprises an amount of the second anticancer drug in the range of about 5% to about 40% (weight/weight) based on the mass ratio of the second anticancer drug to the combined weight of the first anticancer drug and the polymer conjugate.

15. The composition of claim 1, wherein the polymer conjugate comprises an amount of the second anticancer drug in the range of about 10% to about 30% (weight/weight) based on the mass ratio of the second anticancer drug to the combined weight of the first anticancer drug and the polymer conjugate.

16. A method of making the composition of claim 1, comprising the steps of:
   at least partially dissolving the polymer conjugate in a solvent; and
   intermixing the first anticancer drug with the at least partially dissolved polymer conjugate to form a mixture.

17. A method of treating, ameliorating or diagnosing a disease or condition, comprising administering an effective amount of the composition of claim 1 to a mammal in need thereof.

18. The method of claim 17, wherein the disease or condition is selected from the group consisting of lung cancer, breast cancer, colon cancer, ovarian cancer, prostate cancer, and melanoma.

19. The method of claim 17, wherein the disease or condition is melanoma.

20. The method of claim 17, wherein the composition is administered intravenously.

* * * * *